United States Patent
Brent et al.

(12) 
(10) Patent No.: US 6,399,296 B1
(45) Date of Patent: *Jun. 4, 2002

(54) INTERACTION TRAP SYSTEMS FOR DETECTING PROTEIN INTERACTIONS

(75) Inventors: Roger Brent, Cambridge; John M. McCoy, Reading, both of MA (US); Timm H. Jessen, Bad Soden (DE); Chanxing Wilson Xu, Boston, MA (US)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/630,052

(22) Filed: Apr. 9, 1996

Related U.S. Application Data

(63) Continuation-in-part of application No. 08/504,538, filed on Jul. 20, 1995, now Pat. No. 6,004,746, which is a continuation-in-part of application No. 08/278,082, filed on Jul. 20, 1994.

(51) Int. Cl.[7] ............................ C12Q 1/68; G01N 33/53
(52) U.S. Cl. ................................ 435/6; 435/4; 435/7.8; 435/7.1; 436/501
(58) Field of Search ..................... 435/6, 4, 7.1, 69.1, 435/7.8; 436/501, 63, 86

(56) References Cited

U.S. PATENT DOCUMENTS

| | | |
|---|---|---|
| 5,270,181 A | 12/1993 | McCoy et al. |
| 5,283,173 A | 2/1994 | Fields et al. |
| 5,352,660 A | * 10/1994 | Pawson |
| 5,885,780 A | * 3/1999 | Olivera et al. |

FOREIGN PATENT DOCUMENTS

| | | |
|---|---|---|
| EP | 0496162 | 7/1992 |
| WO | WO94/10300 | 5/1994 |

OTHER PUBLICATIONS

Goding (1983) Monoclonal Antibodies: Principles and Practice, Academic Press, Orlando, Fla., pp. 56–97, 40, 156–163, 174–178, 188–207, and 250–261, 1983.*

Chakraborty et al., "Analysis of the Oligomerization of Myogenin and E2A Products in Vivo using a Two–Hybrid Assay System", J. Biol. Chem. 267:17498–17501 (1992).

Chien et al., "The Two–Hybrid System: A Method to Identify and Clone Genes for Proteins that Interact with a Protein of Interest", PNAS USA 88:9578–9582 (1991).

Fields et al., "The Two–Hybrid System: an Assay for Protein—Protein Interactions", Trends in Genetics 10:286–292 (1994).

Harper et al., "The p21 Cdk–Interacting Protein Cip1 is a Potent Inhibitor of G1 Cyclin–Dependent Kinases", Cell 75:805–816 (1993).

Hartley, "Cellular Interactions in Development, A Practical Approach", published 1994 by IRL Press (N.Y.), pp. 153–179.

* cited by examiner

Primary Examiner—Gary L. Kunz
Assistant Examiner—Stephen Gucker
(74) Attorney, Agent, or Firm—Clark & Elbing LLP

(57) ABSTRACT

Disclosed herein is a method of determining whether a first protein is capable of physically interacting with a second protein, involving: (a) providing a host cell which contains (i) a reporter gene operably linked to a protein binding site; (ii) a first fusion gene which expresses a first fusion protein, the first fusion protein including the first protein covalently bonded to a binding moiety which is capable of specifically binding to the protein binding site; and (iii) a second fusion gene which expresses a second fusion protein, the second fusion protein including the second protein covalently bonded to a gene activating moiety and being conformationally-constrained; and (b) measuring expression of the reporter gene as a measure of an interaction between the first and the second proteins. Also disclosed are methods for assaying protein interactions, and identifying antagonists and agonists of protein interactions.

20 Claims, 9 Drawing Sheets

Peptide 13: SVRMRYGIDAFFDLGGLLHG (SEQ ID NO:9)

Peptide 1: ELRHRLGRAL SEDMVRGLAW GPTSHCATVPG TSDLWRVIRFL (SEQ ID NO:10)

Peptide i5-1: YSFVHHGFFNFRVSWREMLA (SEQ ID NO:11)

Peptide i5-4: QVWSLWALGWRWLRRYGWNM (SEQ ID NO:12)

Peptide i5-9: WRRMELDAEIRWVKPISPLE (SEQ ID NO:13)

Peptide 3: LVCKSYRLDW EAGALFRSLF (SEQ ID NO:18)

Peptide 4: YRWQQGVVPS NWASCSFRCG (SEQ ID NO:19)

Peptide 7: SSFSLWLLMV KSIKRAAWEL GPSSAWNTSG WASLADFY (SEQ ID NO:20)

FIG. 3B

| | | | | |
|---|---|---|---|---|
| pep1 | ELRHRLGRAL | SEDMVRGLAW | GPTSHCATVP | GRSDLWRVIR FL | (SEQ ID NO: 10) |
| pep2 | LVCKSYRLDW | EAGALFRSLF | | | (SEQ ID NO: 18) |
| pep3 | YRWQQGVVPS | NMASCSFRCQ | | | (SEQ ID NO: 19) |
| pep4 | SSFSLWLLMV | KSIKRAAWEL | GPSSAWNTSG | WASLSDFY | (SEQ ID NO: 20) |
| pep5 | SVRMRYGIDA | PFDLGGLLHG | | | (SEQ ID NO: 9) |
| pep6 | RVKLGYSFWA | QSLLRCISVG | | | (SEQ ID NO: 21) |
| pep7 | QLYAGCYLGV | VIASSLSIRV | | | (SEQ ID NO: 22) |
| pep8 | YSFVHGFFN | FRVSWREMLA | | | (SEQ ID NO: 11) |
| pep9 | QQRFVFSPSW | FTCAGTSDFW | GPEPLFDWTR | D | (SEQ ID NO: 23) |
| pep10 | QVWSLWALGW | RWLRRYGWNM | | | (SEQ ID NO: 12) |
| pep11 | WRRMELDAEI | RWVKPISPLE | | | (SEQ ID NO: 13) |
| pep12 | RPLTGRWVVW | GRRHEECGLT | | | (SEQ ID NO: 24) |
| pep13 | PVCCMMYGHR | TAPHSVFNVD | | | (SEQ ID NO: 25) |
| pep14 | WSPELLRAMV | AFRWLLERRP | | | (SEQ ID NO: 26) |

FIG. 4B

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
        (A) LENGTH:    2 0
        (B) TYPE:      amino acid
        (C) STRANDEDNESS: Not Relevant
        (D) TOPOLOGY:      linear (xi) SEQUENCE DESCRIPTION: SEQ ID NO:1:

Leu Val Cys Lys Ser Tyr Arg Leu Asp Trp G lu Ala Gly Ala Leu Phe

```
1               5                10               15
Arg Ser Leu Phe
        20
```

(2) INFORMATION FOR SEQ ID NO:2:

(i) SEQUENCE CHARACTERISTICS:
        (A) LENGTH:      2 0
        (B) TYPE:        amino acid
        (C) STRANDEDNESS: Not Relevant
        (D) TOPOLOGY:    linear (xi) SEQUENCE DESCRIPTION: SEQ ID NO:2:

```
Met Val Val Ala Ala Glu Ala Val Arg Thr V al Leu Leu Ala Asp Gly
1               5                10               15
Gly Asp Val Thr
        20
```

(2) INFORMATION FOR SEQ ID NO:3:

(i) SEQUENCE CHARACTERISTICS:
        (A) LENGTH:      2 0
        (B) TYPE:        amino acid
        (C) STRANDEDNESS: Not Relevant
        (D) TOPOLOGY:    linear (xi) SEQUENCE DESCRIPTION: SEQ ID NO:3:

```
Pro Asn Trp Pro His Gln Leu Arg Val Gly A rg Val Leu Trp Glu Arg
1               5                10               15
Leu Ser Phe Glu
        20
```

(2) INFORMATION FOR SEQ ID NO:4:

(i) SEQUENCE CHARACTERISTICS:
        (A) LENGTH:      9 1
        (B) TYPE:        nucleic acid
        (C) STRANDEDNESS: dou ble
        (D) TOPOLOGY:    linear (ix) FEATURE:
        (D) OTHER INFORMATION: N is A or T or G or C; K is G or T.

(xi) SEQUENCE DESCRIPTION: SEQ ID NO:4:

```
GACTGACTGG TCCGNNKNNK NNKNNKNNKN NKNNKNNKNN KNNKNNKNNK N NKNNKNNKN      60

NKNNKNNKNN KNNKGGTCCT CAGTCAGTCA G                                     91
```

(2) INFORMATION FOR SEQ ID NO:5:

(i) SEQUENCE CHARACTERISTICS:
        (A) LENGTH:      1 7
        (B) TYPE:        nucleic acid
        (C) STRANDEDNESS: dou ble
        (D) TOPOLOGY:    linear (xi) SEQUENCE DESCRIPTION: SEQ ID NO:5:

```
CTGACTGACT GAGGACC                                                     17
```

(2) INFORMATION FOR SEQ ID NO:6:

(i) SEQUENCE CHARACTERISTICS:
        (A) LENGTH:      2 4
        (B) TYPE:        amino acid
        (C) STRANDEDNESS: Not Relevant
        (D) TOPOLOGY:    linear

```
   (xi) SEQUENCE DESCRIPTION: SEQ ID NO:6:

Gly Pro Leu Val Cys Lys Ser Tyr Arg Leu A sp Trp Glu Ala Gly Ala
1               5                   10                  15

Leu Phe Arg Ser Leu Phe Gly Pro
            20

(2) INFORMATION FOR SEQ ID NO:7:

(i) SEQUENCE CHARACTERISTICS:
         (A) LENGTH:    2 4
         (B) TYPE:      amino acid
         (C) STRANDEDNESS: Not Relevant
         (D) TOPOLOGY:     linear (xi) SEQUENCE DESCRIPTION: SEQ ID NO:7:

Gly Pro Met Val Val Ala Ala Glu Ala Val A rg Thr Val Leu Leu Ala
1               5                   10                  15

Asp Gly Gly Asp Val Thr Gly Pro
            20

(2) INFORMATION FOR SEQ ID NO:8:

(i) SEQUENCE CHARACTERISTICS:
         (A) LENGTH:    2 4
         (B) TYPE:      amino acid
         (C) STRANDEDNESS: Not Relevant
         (D) TOPOLOGY:     linear (xi) SEQUENCE DESCRIPTION: SEQ ID NO:8:

Gly Pro Pro Asn Trp Pro His Gln Leu Arg V al Gly Arg Val Leu Trp
1               5                   10                  15

Glu Arg Leu Ser Phe Glu Gly Pro
            20

(2) INFORMATION FOR SEQ ID NO:9:

(i) SEQUENCE CHARACTERISTICS:
         (A) LENGTH:    2 0
         (B) TYPE:      amino acid
         (C) STRANDEDNESS: Not Relevant
         (D) TOPOLOGY:     linear (xi) SEQUENCE DESCRIPTION: SEQ ID NO:9:

Ser Val Arg Met Arg Tyr Gly Ile Asp Ala P he Phe Asp Leu Gly Leu
1               5                   10                  15

Leu His Gly
      20

(2) INFORMATION FOR SEQ ID NO:10:

(i) SEQUENCE CHARACTERISTICS:
         (A) LENGTH:    4 2
         (B) TYPE:      amino acid
         (C) STRANDEDNESS: Not Relevant
         (D) TOPOLOGY:     linear (xi) SEQUENCE DESCRIPTION: SEQ ID NO:10:

Glu Leu Arg His Arg Leu Gly Arg Ala Leu S er Glu Asp Met Val Arg Gly
1               5                   10                  15

Leu Ala Trp Gly Pro Thr Ser His Cys Ala T hr Val Pro Gly Thr Ser Asp
        20                  25                  30

Leu Trp Arg Val Ile Arg Phe Leu
35                  40
```

(2) INFORMATION FOR SEQ ID NO:11:

(i) SEQUENCE CHARACTERISTICS:
        (A) LENGTH: 20
        (B) TYPE: amino acid
        (C) STRANDEDNESS: Not Relevant
        (D) TOPOLOGY: linear (xi) SEQUENCE DESCRIPTION: SEQ ID NO:11:

```
Tyr Ser Phe Val His His Gly Phe Phe Asn P he Arg Val Ser Trp Arg Glu
1               5                   10                  15
Met Leu Ala
        20
```

(2) INFORMATION FOR SEQ ID NO:12:

(i) SEQUENCE CHARACTERISTICS:
        (A) LENGTH: 20
        (B) TYPE: amino acid
        (C) STRANDEDNESS: Not Relevant
        (D) TOPOLOGY: linear (xi) SEQUENCE DESCRIPTION: SEQ ID NO:12:

```
Gln Val Trp Ser Leu Trp Ala Leu Gly Trp A rg Trp Leu Arg Arg Tyr Gly
1               5                   10                  15
Trp Asn Met
        20
```

(2) INFORMATION FOR SEQ ID NO:13:

(i) SEQUENCE CHARACTERISTICS:
        (A) LENGTH: 20
        (B) TYPE: amino acid
        (C) STRANDEDNESS: Not Relevant
        (D) TOPOLOGY: linear (xi) SEQUENCE DESCRIPTION: SEQ ID NO:13:

```
Trp Arg Arg Met Glu Leu Asp Ala Glu Ile A rg Trp Val Lys Pro Ile Ser
1               5                   10                  15
Pro Leu Glu
        20
```

(2) INFORMATION FOR SEQ ID NO:14:

(i) SEQUENCE CHARACTERISTICS:
        (A) LENGTH: 31
        (B) TYPE: amino acid
        (C) STRANDEDNESS: Not Relevant
        (D) TOPOLOGY: linear (xi) SEQUENCE DESCRIPTION: SEQ ID NO:14:

```
Arg Arg Ala Ser Val Cys Gly Pro Leu Leu S er Lys Arg Gly Tyr Gly
1               5                   10                  15
Pro Pro Phe Tyr Leu Ala Gly Met Thr Ala P ro Glu Gly Pro Cys
            20                  25                  30
```

(2) INFORMATION FOR SEQ ID NO:15:

(i) SEQUENCE CHARACTERISTICS:
        (A) LENGTH: 30
        (B) TYPE: amino acid
        (C) STRANDEDNESS: Not Relevant
        (D) TOPOLOGY: linear (xi) SEQUENCE DESCRIPTION: SEQ ID NO:15:

```
Arg Arg Ala Ser Val Cys Gly Pro Leu His Tyr Trp Gly Leu Gly Gly
1               5                  10                 15

Phe Val Asp Leu Trp Gln Glu Thr Thr Gly Val Gly Pro Cys
            20                  25              30
```

(2) INFORMATION FOR SEQ ID NO:16:

(i) SEQUENCE CHARACTERISTICS:
        (A) LENGTH: 19
        (B) TYPE: nucleic acid
        (C) STRANDEDNESS: double
        (D) TOPOLOGY: linear (xi) SEQUENCE DESCRIPTION: SEQ ID NO:16:

```
GACGGGGCGA TCCTCGTCG                                           19
```

(2) INFORMATION FOR SEQ ID NO:17:

(i) SEQUENCE CHARACTERISTICS:
        (A) LENGTH: 38
        (B) TYPE: amino acid
        (C) STRANDEDNESS: Not Relevant
        (D) TOPOLOGY: linear (xi) SEQUENCE DESCRIPTION: SEQ ID NO:17:

```
Trp Ala Glu Trp Cys Gly Pro Val Cys Ala His Gly Ser Arg Ser Leu
1               5                  10                 15

Thr Leu Leu Thr Lys Tyr His Val Ser Phe Leu Gly Pro Cys Lys Met
            20                  25              30

Ile Ala Pro Ile Leu Asp
        35
```

(2) INFORMATION FOR SEQ ID NO:18:

(i) SEQUENCE CHARACTERISTICS:
        (A) LENGTH: 20
        (B) TYPE: amino acid
        (C) STRANDEDNESS: Not Relevant
        (D) TOPOLOGY: linear (xi) SEQUENCE DESCRIPTION: SEQ ID NO:18:

```
Leu Val Cys Lys Ser Tyr Arg Leu Asp Trp Glu Ala Gly Ala Leu Phe Arg
1               5                  10                 15

Ser Leu Phe
        20
```

(2) INFORMATION FOR SEQ ID NO:19:

(i) SEQUENCE CHARACTERISTICS:
        (A) LENGTH: 20
        (B) TYPE: amino acid
        (C) STRANDEDNESS: Not Relevant
        (D) TOPOLOGY: linear (xi) SEQUENCE DESCRIPTION: SEQ ID NO:19:

```
Tyr Arg Trp Gln Gln Gly Val Val Pro Ser Asn Trp Ala Ser Cys Ser Phe
1               5                  10                 15

Arg Cys Gly
        20
```

(2) INFORMATION FOR SEQ ID NO:20:

(i) SEQUENCE CHARACTERISTICS:
        (A) LENGTH: 38
        (B) TYPE: amino acid (C) STRANDEDNESS: Not Relevant
            (D) TOPOLOGY:     linear (xi) SEQUENCE DESCRIPTION: SEQ ID NO:20:

Ser Ser Phe Ser Leu Trp Leu Leu Met Val Lys Ser Ile Lys Arg Ala Ala
1               5                   10                  15

Trp Glu Leu Gly Pro Ser Ser Ala Trp Asn Thr Ser Gly Trp Ala Ser Leu
            20                  25                  30

Ala Asp Phe Tyr
35

(2) INFORMATION FOR SEQ ID NO:21:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:21:

Arg Val Lys Leu Gly Tyr Ser Phe Trp Ala Gln Ser Leu Leu Arg Cys
1               5                   10                  15

Ile Ser Val Gly
            20

(2) INFORMATION FOR SEQ ID NO:22:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:22:

Gln Leu Tyr Ala Gly Cys Tyr Leu Gly Val Val Ile Ala Ser Ser Leu
1               5                   10                  15

Ser Ile Arg Val
            20

(2) INFORMATION FOR SEQ ID NO:23:

(i) SEQUENCE CHARACTERISTICS:
            (A) LENGTH: 31 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:23:

Gln Gln Arg Phe Val Phe Ser Pro Ser Trp Phe Thr Cys Ala Gly Thr
1               5                   10                  15

Ser Asp Phe Trp Gly Pro Glu Pro Leu Phe Asp Trp Thr Arg Asp
            20                  25                  30

(2) INFORMATION FOR SEQ ID NO:24:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:24:

Arg Pro Leu Thr Gly Arg Trp Val Val Trp G ly Arg Arg His Glu Glu
 1               5                  10                  15

Cys Gly Leu Thr
            20

(2) INFORMATION FOR SEQ ID NO:25:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:25:

Pro Val Cys Cys Met Met Tyr Gly His Arg T hr Ala Pro His Ser Val
 1               5                  10                  15

Phe Asn Val Asp
            20

(2) INFORMATION FOR SEQ ID NO:26:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:26:

Trp Ser Pro Glu Leu Leu Arg Ala Met Val A la Phe Arg Trp Leu Leu
 1               5                  10                  15

Glu Arg Arg Pro
            20

(2) INFORMATION FOR SEQ ID NO:27:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:27:

TAATGAGCGA TAAACACCAC CACCACCACC ACGACGACGA CGACAAAGG                           49

(2) INFORMATION FOR SEQ ID NO:28:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:28:

TACCTTTGTC GCTGTCGTCG TGGTGGTGGT GGTGGTGTTT ATCGCTCATT A                         51

INTERACTION TRAP SYSTEMS FOR DETECTING PROTEIN INTERACTIONS

CROSS REFERENCE TO RELATED APPLICATIONS

This application is a continuation-in-part of U.S. Ser. No. 08/504,538, filed Jul. 20, 1995 now U.S. Pat. No. 6,004,746, which is a continuation-in-part of U.S. Ser. No. 08/278,082, filed Jul. 20, 1994.

BACKGROUND OF THE INVENTION

This invention relates to methods for detecting protein interactions and isolating novel proteins.

SUMMARY OF THE INVENTION

In general, the invention features methods for detecting interactions among proteins.

Accordingly, in one aspect, the invention features a method of determining whether a first protein is capable of physically interacting with a second protein. The method includes (a) providing a host cell which contains (i) a reporter gene operably linked to a DNA-binding-protein recognition site; (ii) a first fusion gene which expresses a first fusion protein, the first fusion protein comprising the first protein covalently bonded to a binding moiety which is capable of specifically binding to the DNA-binding-protein recognition site; and (iii) a second fusion gene which expresses a second fusion protein, the second fusion protein including the second protein covalently bonded to a gene activating moiety and being conformationally-constrained; and (b) measuring expression of the reporter gene as a measure of an interaction between the first and said second proteins.

Preferably, the second protein is a short peptide of at least 6 amino acids in length and is less than or equal to 60 amino acids in length; includes a randomly generated or intentionally designed peptide sequence; includes one or more loops; or is conformationally-constrained as a result of covalent bonding to a conformation-constraining protein, e.g., thioredoxin or a thioredoxin-like molecule. Where the second protein is covalently bonded to a conformationally constraining protein the invention features a polypeptide wherein the second protein is embedded within the conformation-constraining protein to which it is covalently bonded. Where the conformation-constraining protein is thioredoxin, the invention also features an additional method which includes a second protein which is conformationally-constrained by disulfide bonds between cysteine residues in the amino-terminus and in the carboxy-terminus of the second protein.

In another aspect, the invention features a method of detecting an interacting protein in a population of proteins, comprising: (a) providing a host cell which contains (i) a reporter gene operably linked to a DNA-binding-protein recognition site; and (ii) a fusion gene which expresses a fusion protein, the fusion protein including a test protein covalently bonded to a binding moiety which is capable of specifically binding to the DNA-binding-protein recognition site; (b) introducing into the host cell a second fusion gene which expresses a second fusion protein, the second fusion protein including one of said population of proteins covalently bonded to a gene activating moiety and being conformationally-constrained; and (c) measuring expression of the reporter gene. Preferably, the population of proteins includes short peptides of between 1 and 60 amino acids in length.

The invention also features a method of detecting an interacting protein within a population wherein the population of proteins is a set of randomly generated or intentionally designed peptide sequences, or where the population of proteins is conformationally-constrained by covalently bonding to a conformation-constraining protein. Preferably, where the population of proteins is conformationally-constrained by covalent bonding to a conformation-constraining protein, the population of proteins is embedded within the conformation-constraining protein. The invention further features a method of detecting an interacting protein within a population wherein the conformation-constraining protein is thioredoxin. Preferably, the population of proteins is inserted into the active site loop of the thioredoxin.

The invention further features a method wherein each of the population of proteins is conformationally-constrained by disulfide bonds between cysteine residues in the amino-terminus and in the carboxy-terminus of said protein.

In preferred embodiments of various aspects, the host cell is yeast; the DNA binding domain is LexA; the interacting protein includes one or more loops; and/or the reporter gene is assayed by a color reaction or by cell viability.

In other embodiments the bait may be Cdk2 or a Ras protein sequence.

In another related aspect, the invention features a method of identifying a candidate interactor. The method includes (a) providing a reporter gene operably linked to a DNA-binding-protein recognition site; (b) providing a first fusion protein, which includes a first protein covalently bonded to a binding moiety which is capable of specifically binding to the DNA-binding-protein recognition site; (c) providing a second fusion protein, which includes a second protein covalently bonded to a gene activating moiety and being conformationally-constrained, the second protein being capable of interacting with said first protein; (d) contacting said candidate interactor with said first protein and/or said second protein; and (e) measuring expression of said reporter gene.

The invention features a method of identifying a candidate interactor wherein the first fusion protein is provided by providing a first fusion gene which expresses the first fusion protein and wherein the second fusion protein is provided by providing a second fusion gene which expresses said second fusion protein. Alternatively, the reporter gene, the first fusion gene, and the second fusion gene are included on a single piece of DNA.

The invention also features a method of identifying candidate interactors wherein the first fusion protein and the second fusion protein are permitted to interact prior to contact with said candidate interactor, and a related method wherein the first fusion protein and the candidate interactor are permitted to interact prior to contact with said second fusion protein.

In a preferred embodiment, the candidate interactor is conformationally-constrained and may include one or more loops. Where the candidate interactor is an antagonist, reporter gene expression is reduced. Where the candidate interactor is an agonist, reporter gene expression is increased. The candidate interactor is a member selected from the group consisting of proteins, polynucleotides, and small molecules. In addition, a candidate interactor can be encoded by a member of a cDNA or synthetic DNA library. Moreover, the candidate interactor can be a mutated form of said first fusion protein or said second fusion protein.

In a preferred embodiment of any of the above aspects, the candidate interactor is isolated in vitro and shown to function in vivo, i.e., as a conformationally constrained intracellular peptide.

In a related aspect, the invention features a population of eukaryotic cells, each cell having a recombinant DNA molecule encoding a conformationally-constrained intracellular peptide, there being at least 100 different recombinant molecules in the population, each molecule being in at least one cell of said population.

Preferably, the intracellular peptides within the population of cells are conformationally-constrained because they are covalently bonded to a conformation-constraining protein.

In preferred embodiments the intracellular peptide is embedded within the conformation-constraining protein, preferably thioredoxin; the intracellular peptide is conformationally-constrained by disulfide bonds between cysteine residues in the amino-terminus and in the carboxy-terminus of said second protein; the intracellular peptide includes one or more loops; the population of eukaryotic cells are yeast cells; the recombinant DNA molecule further encodes a gene activating moiety covalently bonded to said intracellular peptide; and/or the intracellular peptide physically interacts with a second recombinant protein inside said eukaryotic cells.

In another aspect, the invention features a method of assaying an interaction between a first protein and a second protein. The method includes: (a) providing a reporter gene operably linked to a DNA-binding-protein recognition site; (b) providing a first fusion protein including a first protein covalently bonded to a binding moiety which is capable of specifically binding to the DNA-binding-protein recognition site; (c) providing a second fusion protein including a second protein which is conformationally constrained (and may include one or more loops) and is covalently bonded to a gene activating moiety; (d) combining the reporter gene, the first fusion protein, and the second fusion protein; and (e) measuring expression of the reporter gene.

In a preferred embodiment, the invention further features a method of assaying the interaction between two proteins wherein the first fusion protein is provided by providing a first fusion gene which expresses the first fusion protein and wherein the second fusion protein is provided by providing a second fusion gene which expresses the second fusion protein. In another preferred embodiment, the interaction is assayed in vitro and shown to function in vivo, i.e., as a conformationally constrained intracellular peptide.

In yet other aspects, the invention features a protein including the sequence Leu-Val-Cys-Lys-Ser-Tyr-Arg-Leu-Asp-Trp-Glu-Ala-Gly-Ala-Leu-Phe-Arg-Ser-Leu-Phe (SEQ ID NO: 1), preferably conformationally-constrained; protein including the sequence Met-Val-Val-Ala-Ala-Glu-Ala-Val-Arg-Thr-Val-Leu-Leu-Ala-Asp-Gly-Gly-Asp-Val-Thr (SEQ ID NO: 2); preferably conformationally-constrained; a protein including the sequence Pro-Asn-Trp-Pro-His-Gln-Leu-Arg-Val-Gly-Arg-Val-Leu-Trp-Glu-Arg-Leu-Ser-Phe-Glu (SEQ ID NO: 3), preferably conformationally-constrained; a protein including the sequence Ser-Val-Arg-Met-Arg-Tyr-Gly-Ile-Asp-Ala-Phe-Phe-Asp-Leu-Gly-Gly-Leu-Leu-His-Gly (SEQ ID NO: 9), preferably conformationally-constrained; a protein including the sequence Glu-Leu-Arg-His-Arg-Leu-Gly-Arg-Ala-Leu-Ser-Glu-Asp-Met-Val-Arg-Gly-Leu-Ala-Trp-Gly-Pro-Thr-Ser-His-Cys-Ala-Thr-Val-Pro-Gly-Thr-Ser-Asp-Leu-Trp-Arg-Val-Ile-Arg-Phe-Leu (SEQ ID NO: 10), preferably conformationally-constrained; a protein including the sequence Tyr-Ser-Phe-Val-His-His-Gly-Phe-Phe-Asn-Phe-Arg-Val-Ser-Trp-Arg-Glu-Met-Leu-Ala (SEQ ID NO: 11), preferably conformationally-constrained; a protein including the sequence Gln-Val-Trp-Ser-Leu-Trp-Ala-Leu-Gly-Trp-Arg-Trp-Leu-Arg-Arg-Tyr-Gly-Trp-Asn-Met (SEQ ID NO: 12), preferably conformationally-constrained; a protein including the sequence Trp-Arg-Arg-Met-Glu-Leu-Asp-Ala-Glu-Ile-Arg-Trp-Val-Lys-Pro-Ile-Ser-Pro-Leu-Glu (SEQ ID NO: 13), preferably conformationally-constrained; a protein including the sequence Trp-Ala-Glu-Trp-Cys-Gly-Pro-Val-Cys-Ala-His-Gly-Ser-Arg-Ser-Leu-Thr-Leu-Leu-Thr-Lys-Tyr-His-Val-Ser-Phe-Leu-Gly-Pro-Cys-Lys-Met-Ile-Ala-Pro-Ile-Leu-Asp (SEQ ID NO:17), preferably conformationally-constrained; a protein including the sequence Leu-Val-Cys-Lys-Ser-Tyr-Arg-Leu-Asp-Trp-Glu-Ala-Gly-Ala-Leu-Phe-Arg-Ser-Leu-Phe (SEQ ID NO: 18), preferably conformationally-constrained; a protein including the sequence Tyr-Arg-Trp-Gln-Gln-Gly-Val-Val-Pro-Ser-Asn-Trp-Ala-Ser-Cys-Ser-Phe-Arg-Cys-Gly (SEQ ID NO: 19), preferably conformationally-constrained; a protein including the sequence Ser-Ser-Phe-Ser-Leu-Trp-Leu-Leu-Met-Val-Lys-Ser-Ile-Lys-Arg-Ala-Ala-Trp-Glu-Leu-Gly-Pro-Ser-Ser-Ala-Trp-Pro-Asn-Thr-Ser-Gly-Trp-Ala-Ser-Leu-Ala-Ala-Asp-Phe-Tyr (SEQ ID NO: 20) preferably conformationally-constrained; a protein including the sequence Arg-Val-Lys-Leu-Gly-Tyr-Ser-Phe-Trp-Ala-Gln-Ser-Leu-Leu-Arg-Cys-Ile-Ser-Val-Gly (SEQ ID NO: 21), preferably conformationally-constrained; a protein including the sequence Gln-Leu-Tyr-Ala-Gly-Cys-Tyr-Leu-Gly-Val-Val-Ile-Ala-Ser-Ser-Leu-Ser-Ile-Arg-Val (SEQ ID NO: 22), preferably conformationally-constrained; a protein including the sequence Gln-Gln-Arg-Phe-Val-Phe-Ser-Pro-Ser-Trp-Phe-Thr-Cys-Ala-Gly-Thr-Ser-Asp-Phe-Trp-Gly-Pro-Glu-Pro-Leu-Phe-Asp-Trp-Thr-Arg-Asp (SEQ ID NO: 23), preferably conformationally-constrained; a protein including the sequence Arg-Pro-Leu-Thr-Gly-Arg-Trp-Val-Val-Trp-Gly-Arg-Arg-His-Glu-Glu-Cys-Gly-Leu-Thr (SEQ ID NO: 24), preferably conformationally-constrained; a protein including the sequence Pro-Val-Cys-Cys-Met-Met-Tyr-Gly-His-Arg-Thr-Ala-Pro-His-Ser-Val-Phe-Asn-Val-Asp (SEQ ID NO: 25), preferably conformationally-constrained; a protein including the sequence Trp-Ser-Pro-Glu-Leu-Leu-Arg-Ala-Met-Val-Ala-Phe-Arg-Trp-Leu-Leu-Glu-Arg-Arg-Pro (SEQ ID NO: 26); and substantially pure DNA encoding the immediately foregoing proteins.

The invention also includes novel proteins and other candidate interactors identified by the foregoing methods. It will be appreciated that these proteins and candidate interactors may either increase or decrease reporter gene activity and that these changes in activity may be measured using assays described herein or known in the art. Also included in the invention are methods for using conformationally constrained interactor proteins. For example, the conformationally constrained proteins of the invention may be used as reagents in assays for protein detection that involve formation of a complex between the conformationally constrained protein and a protein of interest to which it specifically binds, followed by complex detection (for example, by an immunoprecipitation, Western blot, or affinity column technique that utilizes the conformationally constrained protein as the complex-forming reagent).

Finally, the invention features a method of assaying an interaction between a first protein and a second protein, involving: (a) providing the first protein; (b) providing a fusion protein including the second protein, the second protein being conformationally-constrained; (c) contacting the first protein with the fusion protein under conditions which allow complex formation; (d) detecting the complex as an indication of an interaction; and (e) determining whether the first protein interacts with the fusion protein inside a cell.

As used herein, by "reporter gene" is meant a gene whose expression may be assayed; such genes include, without limitation, lacZ, amino acid biosynthetic genes, e.g. the yeast LEU2, HIS3, LYS2, TRP1, or URA3 genes, nucleic acid biosynthetic genes, the mammalian chloramphenicol transacetylase (CAT) gene, or any surface antigen gene for which specific antibodies are available. Reporter genes may encode any protein that provides a phenotypic marker, for example, a protein that is necessary for cell growth or a toxic protein leading to cell death, or may encode a protein detectable by a color assay leading to the presence or absence of color (e.g., florescent proteins and derivatives thereof). Alternatively, a reporter gene may encode a suppressor tRNA, the expression of which produces a phenotype that can be assayed. A reporter gene according to the invention includes elements (e.g., all promoter elements) necessary for reporter gene function.

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By "covalently bonded" is meant that two domains are joined by covalent bonds, directly or indirectly. That is, the "covalently bonded" proteins or protein moieties may be immediately contiguous or may be separated by stretches of one or more amino acids within the same fusion protein.

By "providing" is meant introducing the fusion proteins into the interaction system sequentially or simultaneously, and directly (as proteins) or indirectly (as genes encoding those proteins).

By "protein" is meant a sequence of amino acids of any length, constituting all or a part of a naturally-occurring polypeptide or peptide, or constituting a non-naturally-occurring polypeptide or peptide (e.g., a randomly generated peptide sequence or one of an intentionally designed collection of peptide sequences).

By a "binding moiety" is meant a stretch of amino acids which is capable of directing specific polypeptide binding to a particular DNA sequence (i.e., a "DNA-binding-protein recognition site").

By "weak gene activating moiety" is meant a stretch of amino acids which is capable of weakly inducing the expression of a gene to whose control region it is bound. As used herein, "weakly" is meant below the level of activation effected by GAL4 activation region II (Ma and Ptashne, Cell 48:847, 1987) and is preferably at or below the level of activation effected by the B112 activation domain of Ma and Ptashne (Cell 51:113, 1987). Levels of activation may be measured using any downstream reporter gene system and comparing, in parallel assays, the level of expression stimulated by the GAL4 region II-polypeptide with the level of expression stimulated by the polypeptide to be tested.

By "altering the expression of the reporter gene" is meant an increase or decrease in the expression of the reporter gene to the extent required for detection of a change in the assay being employed. It will be appreciated that the degree of change will vary depending upon the type of reporter gene construct or reporter gene expression assay being employed.

By "conformationally-constrained" is meant a protein that has reduced structural flexibility because its amino and carboxy termini are fixed in space. As a result of this constraint, the protein may form "loops" (i.e., regions of amino acids of any shape which extend away from the constrained amino and carboxy termini). Preferably, the conformationally-constrained protein is displayed in a structurally rigid manner. Conformational constraint according to the invention may be brought about by exploiting the disulfide-bonding ability of a natural or recombinantly-introduced pair of cysteine residues, one residing at or near the amino-terminal end of the protein of interest and the other at or near the carboxy-terminal end. Alternatively, conformational constraint may be facilitated by embedding the protein of interest within a conformation-constraining protein.

By "conformation-constraining protein" is meant any peptide or polypeptide which is capable of reducing the flexibility of another protein's amino and/or carboxy termini. Preferably, such proteins provide a rigid scaffold or platform for the protein of interest. In addition, such proteins preferably are capable of providing protection from proteolytic degradation and the like, and/or are capable of enhancing solubility. Examples of conformation-constraining proteins include thioredoxin and other thioredoxin-like proteins, nucleases (e.g., RNase A), proteases (e.g., trypsin), protease inhibitors (e.g., bovine pancreatic trypsin inhibitor), antibodies or structurally-rigid fragments thereof, conotoxins, and the pleckstrin homology domain. A conformation-constraining peptide can be of any appropriate length and can even be a single amino acid residue.

"Thioredoxin-like proteins" are defined herein as amino acid sequences substantially similar, e.g., having at least 18% homology, with the amino acid sequence of *E. coli* thioredoxin over an amino acid sequence length of 80 amino acids. Alternatively, a thioredoxin-like DNA sequence is defined herein as a DNA sequence encoding a protein or fragment of a protein characterized by having a three dimensional structure substantially similar to that of human or *E. coli* thioredoxin, e.g., glutaredoxin and optionally by containing an active-site loop. The DNA sequence of glutaredoxin is an example of a thioredoxin-like DNA sequence which encodes a protein that exhibits such substantial similarity in three-dimensional conformation and contains a Cys . . . Cys active-site loop. The amino acid sequence of *E. coli* thioredoxin is described in Eklund et al., EMBO J. 3:1443–1449 (1984). The three-dimensional structure of *E. coli* thioredoxin is depicted in FIG. 2 of Holmgren, J. Biol. Chem. 264:13963–13966 (1989). A DNA sequence encoding the *E. coli* thioredoxin protein is set forth in Lim et al., J. Bacteriol., 163:311–316 (1985). The three dimensional structure of human thioredoxin is described in Forman-Kay et al., Biochemistry 30:2685–98 (1991). A comparison of the three dimensional structures of *E. coli* thioredoxin and glutaredoxin is published in Xia, Protein Science I:310–321 (1992). These four publications are incorporated herein by reference for the purpose of providing information on thioredoxin-like proteins that is known to one of skill in the art. Examples of thioredoxin-like proteins are described herein.

By "candidate interactors" is meant proteins ("candidate interacting proteins") or compounds which physically interact with a protein of interest; this term also encompasses agonists and antagonists. Agonist interactors are identified as compounds or proteins that have the ability to increase reporter gene expression mediated by a pair of interacting proteins. Antagonist interactors are identified as compounds or proteins that have the ability to decrease reporter gene expression mediated by a pair of interacting proteins. Candidate interactors also include so-called peptide "aptamers" which specifically recognize target proteins and may be used in a manner analogous to antibody reagents; such aptamers may include one or more loops.

"Compounds" include small molecules, generally under 1000 MW, carbohydrates, polynucleotides, lipids, and the like.

By "test protein" is meant one of a pair of interacting proteins, the other member of the pair generally referred to as a "candidate interactor" (supra).

By "randomly generated" is meant sequences having no predetermined sequence; this is contrasted with "intentionally designed" sequences which have a DNA or protein sequence or motif determined prior to their synthesis.

By "mutated" is meant altered in sequence, either by site-directed or random mutagenesis. A mutated form of a protein encompasses point mutations as well as insertions, deletions, or rearrangements.

By "intracellular" is meant that the peptide is localized inside the cell, rather than on the cell surface.

By an "activated Ras" is meant any mutated form of Ras which remains bound to GTP for a period of time longer than that exhibited by the corresponding wild-type form of the protein. By "Ras" is meant any form of Ras protein including, without limitation, N-ras, K-ras, and H-ras.

The interaction trap systems described herein provide advantages over more conventional methods for isolating interacting proteins or genes encoding interacting proteins. For example, applicants' systems provide rapid and inexpensive methods having very general utility for identifying and purifying genes encoding a wide range of useful proteins based on the protein's physical interaction with a second polypeptide. This general utility derives in part from the fact that the components of the systems can be readily modified to facilitate detection of protein interactions of widely varying affinity (e.g., by using reporter genes which differ quantitatively in their sensitivity to a protein interaction). The inducible nature of the promoter used to express the interacting proteins also increases the scope of candidate interactors which may be detected since even proteins whose chronic expression is toxic to the host cell may be isolated simply by inducing a short burst of the protein's expression and testing for its ability to interact and stimulate expression of a reporter gene.

If desired, detection of interacting proteins may be accomplished through the use of weak gene activation domain tags. This approach avoids restrictions on the pool of available candidate interacting proteins which may be associated with stronger activation domains (such as GAL4 or VP16); although the mechanism is unclear, such a restriction apparently results from low to moderate levels of host cell toxicity mediated by the strong activation domain.

In addition, the claimed methods make use of conformationally-constrained proteins (i.e., proteins with reduced flexibility due to constraints at their amino and carboxy termini). Conformational constraint may be brought about by embedding the protein of interest within a conformation-constraining protein (i.e., a protein of appropriate length and amino acid composition to be capable of locking the candidate interacting protein into a particular three-dimensional structure). Examples of conformation-constraining proteins include, but are not limited to, thioredoxin (or other thioredoxin-like proteins), nucleases (e.g., RNase A), proteases (e.g., trypsin), protease inhibitors (e.g., bovine pancreatic trypsin inhibitor), antibodies or structurally-rigid fragments thereof, conotoxins, and the pleckstrin homology domain.

Alternatively, conformational constraint may be accomplished by exploiting the disulfide-bonding ability of a natural or recombinantly-introduced pair of cysteine residues, one residing at the amino terminus of the protein of interest and the other at its carboxy terminus. Such disulfide bonding locks the protein into a rigid and therefore conformationally-constrained loop structure. Disulfide bonds between amino-terminal and carboxy-terminal cysteines may be formed, for example, in the cytoplasm of $E.$ $coli$ trxB mutant strains. Under some conditions disulfide bonds may also form within the cytoplasm and nucleus of higher organisms harboring equivalent mutations, for example, an $S.$ $cerevisiae$ YTR4$^-$ mutant strain (Furter et al., Nucl Acids Res. 14:6357–6373, 1986; GenBank Accession Number P29509). In addition, the thioredoxin fusions described herein (trxA fusions) are amenable to this alternative means of introducing conformational constraint, since the cysteines at the base of peptides inserted within the thioredoxin active-site loop are at a proper distance from one another to form disulfide bonds under appropriate conditions.

Conformationally-constrained proteins as candidate interactors are useful in the invention because they are amenable to tertiary structural analysis, thus facilitating the design of simple organic molecule mimetics with improved pharmacological properties. For example, because thioredoxin has a known structure, the protein structure between the conformationally constrained regions may be more easily solved using methods such as NMR and X-ray difference analysis. Certain conformation-constraining proteins also protect the embedded protein from cellular degradation and/or increase the protein's solubility, and/or otherwise alter the capacity of the candidate interactor to interact.

Once isolated, interacting proteins can also be analyzed using the interaction trap system, with the signal generated by the interaction being an indication of any change in the proteins' interaction capabilities. In one particular example, an alteration is made (e.g., by standard in vivo or in vitro directed or random mutagenesis procedures) to one or both of the interacting proteins, and the effect of the alteration(s) is monitored by measuring reporter gene expression. Using this technique, interacting proteins with increased or decreased interaction potential are isolated. Such proteins are useful as therapeutic molecules (for example, agonists or antagonists) or, as described above, as models for the design of simple organic molecule mimetics.

Protein agonists and antagonists may also be readily identified and isolated using a variation of the interaction trap system. In particular, once a protein-protein interaction has been recorded, an additional DNA coding for a candidate agonist or antagonist, or preferably, one of a library of potential agonist- or antagonist-encoding sequences is introduced into the host cell, and reporter gene expression is measured. Alternatively, candidate interactor agonist or antagonist compounds (i.e., including polypeptides as well as non-proteinaceous compounds, e.g., single stranded polynucleotides) are introduced into an in vivo or in vitro interaction trap system according to the invention and their ability to effect reporter gene expression is measured. A decrease in reporter gene expression (compared to a control lacking the candidate sequence or compound) indicates an antagonist. Conversely, an increase in reporter gene expression (compared again to a control) indicates an agonist. Interaction agonists and antagonists are useful as therapeutic agents or as models to design simple mimetics; if desired, an agonist or antagonist protein may be conformationally-constrained to provide the advantages described herein. Particular examples of interacting proteins for which antagonists or agonists may be identified include, but are not limited to, the IL-6 receptor-ligand pair, TGF-β receptor-ligand pair, IL-1 receptor-ligand pair and other receptor-ligand interactions, protein kinase-substrate pairs, interacting pairs of transcription factors, interacting components of signal transduction pathways (for example, cytoplasmic domains of certain receptors and G-proteins), pairs of interacting proteins involved in cell cycle regulation (for example, p16 and CDK4), and neurotransmitter pairs.

Also included in the present invention are libraries encoding conformationally-constrained proteins. Such libraries (which may include natural as well as synthetic DNA sequence collections) are expressed intracellularly or, optionally, in cell-free systems, and may be used together with any standard genetic selection or screen or with any of a number of interaction trap formats for the identification of interacting proteins, agonist or antagonist proteins, or proteins that endow a cell with any identifiable characteristic, for example, proteins that perturb cell cycle progression. Accordingly, peptide-encoding libraries (either random or designed) can be used in selections or screens which either are or are not transcriptionally-based. These libraries (which preferably include at least 100 different peptide-encoding species and more preferably include 1000, or 100,000 or greater individual species) may be transformed into any useful prokaryotic or eukaryotic host, with yeast representing the preferred host. Alternatively, such peptide-encoding libraries may be expressed in cell-free systems.

Other features and advantages of the invention will be apparent from the following detailed description thereof, and from the claims.

BRIEF DESCRIPTION OF THE DRAWINGS

The drawings are first briefly described.

FIG. 3B illustrates the sequence of exemplary Cdk2 interacting peptides.

FIG. 4B illustrates the sequence of the exemplary Cdk2 interacting peptide aptamers assayed in FIG. 4A.

DETAILED DESCRIPTION

Applicants have developed a novel interaction trap system for the identification and analysis of conformationally-constrained proteins that either physically interact with a second protein of interest or that antagonize or agonize such an interaction. In one embodiment, the system involves a eukaryotic host strain (e.g., a yeast strain) which is engineered to produce a protein of therapeutic or diagnostic interest as a fusion protein covalently bonded to a known DNA binding domain; this protein is referred to as a "bait" protein because its purpose in the system is to "catch" useful, but as yet unknown or uncharacterized, interacting polypeptides (termed the "prey"; see below). The eukaryotic host strain also contains one or more "reporter genes," i.e., genes whose transcription is detected in response to a bait-prey interaction. Bait proteins, via their DNA binding domain, bind to their specific DNA recognition site upstream of a reporter gene; reporter transcription is not stimulated, however, because the bait protein lacks an activation domain.

To isolate DNA sequences encoding novel interacting proteins, members of a DNA expression library (e.g., a cDNA or synthetic DNA library, either random or intentionally biased) are introduced into the strain containing the reporter gene and bait protein; each member of the library directs the synthesis of a candidate interacting protein fused to an invariant gene activation domain tag. Those library-encoded proteins that physically interact with the promoter-bound bait protein are referred to as "prey" proteins. Such bound prey proteins (via their activation domain tag) detectably activate the expression of the downstream reporter gene and provide a ready assay for identifying a particular DNA clone encoding an interacting protein of interest. In the instant invention, each candidate prey protein is conformationally-constrained (for example, either by embedding the protein within a conformation-constraining protein or by linking together the protein's amino and carboxy termini). Such a protein is maintained in a fixed, three-dimensional structure, facilitating mimetic drug design.

Figure 1A:
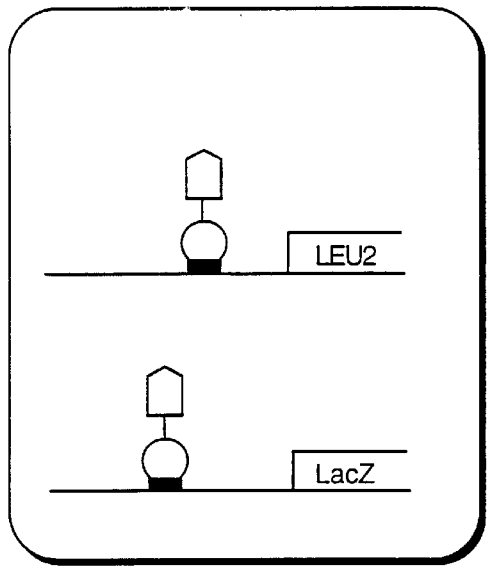
FIGS. 1A–1C illustrate one interaction trap system according to the invention.
Figure 1B:
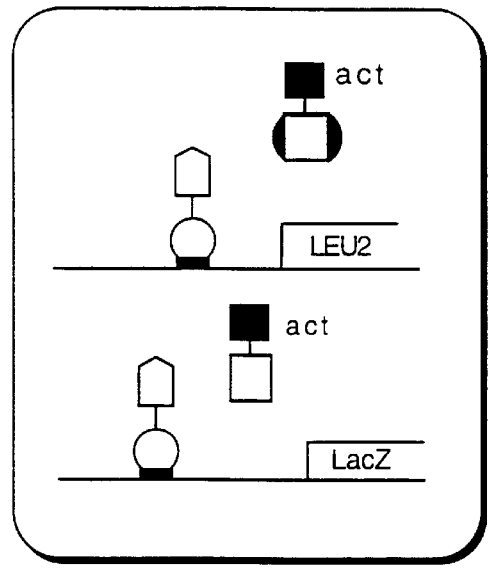
Figure 1C:
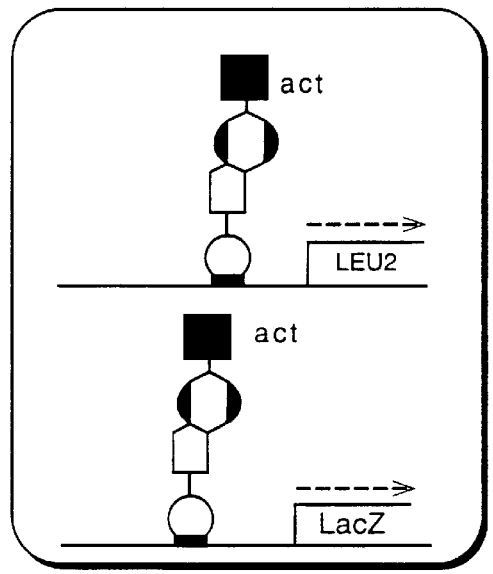

An example of one interaction trap system according to the invention is shown in FIGS. 1A–C. FIG. 1A shows a leucine auxotroph yeast strain containing two reporter genes, LexAop-LEU2 and LexAop-lacZ, and a constitutively expressed bait protein gene. The bait protein (shown as a pentagon) is fused to a DNA binding domain (shown as a circle). The DNA binding protein recognizes and binds a specific DNA-binding-protein recognition site (shown as a solid rectangle) operably-linked to a reporter gene. In FIGS. 1B and 1C, the cells additionally contain candidate prey proteins (candidate interactors) (shown as an empty rectangle in 1B and an empty hexagon in 1C) fused to an activation domain (shown as a solid square); each prey protein is embedded in a conformation-constraining protein (shown as two solid half circles). FIG. 1B shows that if the candidate prey protein does not interact with the transcriptionally-inert LexA-fusion bait protein, the reporter genes are not transcribed; the cell cannot grow into a colony on leu⁻ medium, and it is white on Xgal medium because it contains no β-galactosidase activity. FIG. 1C shows that, if the candidate prey protein interacts with the bait, both reporter genes are active; the cell forms a colony on leu⁻ medium, and cells in that colony have β-galactosidase activity and are blue on Xgal medium. Preferably, in this system, the bait protein (i.e., the protein containing a site-specific DNA binding domain) is transcriptionally inert, and the reporter genes (which are bound by the bait protein) have essentially no basal transcription.

Each component of the system is now described in more detail.

Bait Proteins

The selection host strain depicted in FIGS. 1A–C contains a DNA encoding a bait protein fused to a DNA encoding a DNA binding moiety derived from the bacterial LexA protein. The use of a LexA DNA binding domain provides certain advantages. For example, in yeast, the LexA moiety contains no activation function and has no known effect on transcription of yeast genes (Brent and Ptashne, Nature 312:612–615, 1984; Brent and Ptashne, Cell 43:729–736, 1985). In addition, use of the LexA rather than, for example, the GAL4 DNA-binding domain allows conditional expression of prey proteins in response to galactose induction; this facilitates detection of prey proteins that might be toxic to the host cell if expressed continuously. Finally, the use of a well-defined system, such as LexA, allows knowledge regarding the interaction between LexA and the LexA binding site (i.e., the LexA operator) to be exploited for the purpose of optimizing operator occupancy and/or optimizing the geometry of the bound bait protein to effect maximal gene activation.

Preferably, the bait protein also includes a LexA dimerization domain; this optional domain facilitates efficient LexA dimer formation. Because LexA binds its DNA binding site as a dimer, inclusion of this domain in the bait protein also optimizes the efficiency of operator occupancy (Golemis and Brent, Mol. Cell Biol. 12:3006–3014, (1992)).

LexA represents a preferred DNA binding domain in the invention. However, any other transcriptionally-inert or essentially transcriptionally-inert DNA binding domain may be used in the interaction trap system; such DNA binding domains are well known and include the DNA binding portions of the proteins ACE1 (CUP1), lambda cI, lac repressor, jun, fos, GCN4, or the Tet repressor. The GAL4 DNA binding domain represents a slightly less preferred DNA binding moiety for the bait proteins.

Bait proteins may be chosen from any protein of interest and includes proteins of unknown, known, or suspected diagnostic, therapeutic, or pharmacological importance. Preferred bait proteins include oncoproteins (such as myc, particularly the C-terminus of myc, ras, src, fos, and particularly the oligomeric interaction domains of fos) or any other proteins involved in cell cycle regulation (such as kinases, phosphatases, the cytoplasmic portions of membrane-associated receptors). Particular examples of preferred bait proteins include cyclin and cyclin dependent kinases (for example, Cdk2) or receptor-ligand pairs, or neurotransmitter pairs, or pairs of other signalling proteins. In each case, the protein of interest is fused to a known DNA binding domain as generally described herein. Examples are provided below using Cdk2 and Ras baits.

Reporters

As shown in FIG. 1B, one preferred host strain according to the invention contains two different reporter genes, the LEU2 gene and the lacZ gene, each carrying an upstream binding site for the bait protein. The reporter genes depicted in FIG. 1B each include, as an upstream binding site, one or more LexA operators in place of their native Upstream Activation Sequences (UASs). These reporter genes may be integrated into the chromosome or may be carried on autonomously replicating plasmids (e.g., yeast 2$\mu$ plasmids).

A combination of two such reporters is preferred in the in vivo embodiments of the invention for a number of reasons. First, the LexAop-LEU2 construction allows cells that contain interacting proteins to select themselves by growth on medium that lacks leucine, facilitating the examination of large numbers of potential candidate interactor protein-containing cells. Second, the LexAop-lacZ reporter allows LEU$^+$ cells to be quickly screened to confirm an interaction. And, third, among other technical considerations, the LexAop-LEU2 reporter provides an extremely sensitive first selection, while the LexAop-lacZ reporter allows discrimination between proteins of different interaction affinities.

Although the reporter genes described herein represent a preferred embodiment of the invention, other equivalent genes whose expression may be detected or assayed by standard techniques may also be employed in conjunction with, or instead of, the LEU2 and lacZ genes. Generally, such reporter genes encode an enzyme that provides a phenotypic marker, for example, a protein that is necessary for cell growth or a toxic protein leading to cell death, or encoding a protein detectable by a color assay or because its expression leads to the presence or absence of color. Alternatively, the reporter gene may encode a suppressor tRNA whose expression may be assayed, for example, because it suppresses a lethal host cell mutation. Particular examples of other useful genes whose transcription can be detected include amino acid and nucleic acid biosynthetic genes (such as yeast HIS3, URA3, TRP1, and LYS2) GAL1, *E. coli* galK (which complements the yeast GAL1 gene), and the reporter genes CAT, GUS, florescent proteins and derivatives thereof, and any gene encoding a cell surface antigen for which antibodies are available (e.g., CD4). Reporter genes may be assayed by either qualitative or quantitative means to distinguish candidate interactors as agonists or antagonists.

Prey proteins

In the selection described herein, another DNA construction is utilized which encodes a series of candidate interacting proteins (i.e., prey proteins); each is conformationally-constrained, either by being embedded in a conformation-constraining protein or because the prey protein's amino and carboxy termini are linked (e.g., by disulfide bonding). An exemplary prey protein includes an invariant N-terminal moiety carrying, amino to carboxy terminal, an ATG for protein expression, an optional nuclear localization sequence, a weak activation domain (e.g., the B112 or B42 activation domains of Ma and Ptashne; Cell 51:113, 1987), and an optional epitope tag for rapid immunological detection of fusion protein synthesis. Library sequences, random or intentionally designed synthetic DNA sequences, or sequences encoding conformationally-constrained proteins, may be inserted downstream of this N-terminal fragment to produce fusion genes encoding prey proteins.

Prey proteins other than those described herein are also useful in the invention. For example, cDNAs may be constructed from any mRNA population and inserted into an equivalent expression vector. Such a library of choice may be constructed de novo using commercially available kits (e.g., from Stratagene, La Jolla, Calif.) or using well established preparative procedures (see, e.g., *Current Protocols in Molecular Biology*, New York, John Wiley & Sons, 1987). Alternatively, a number of cDNA libraries (from a number of different organisms) are publicly and commercially available; sources of libraries include, e.g., Clontech (Palo Alto, Calif.) and Stratagene (La Jolla, Calif.). It is also noted that prey proteins need not be naturally occurring full-length polypeptides. In preferred embodiments, prey proteins are encoded by synthetic DNA sequences, are the products of randomly generated open reading frames, are open reading frames synthesized with an intentional sequence bias, or are portions thereof. Preferably, such short randomly generated sequences encode peptides between 1 (and preferably, 6) and 60 amino acids in length. In one particular example, the prey protein includes only an interaction domain; such a domain may be useful as a therapeutic to modulate bait protein activity (i.e., as an antagonist or agonist). In another particular example, the prey protein contains one or more loops. Such a prey protein may be used as an immunological reagent for diagnostic purposes or for any of the therapeutic purposes described herein; in this context, the different loops may recognize different portions of the bait protein and may increase specificity. In addition, a prey protein may be a combination of multiple interacting peptides connected in reading frame (if desired, with alternating conformation-constraining sequences) to provide a further optimized prey protein. In one example, each of these interacting peptides constitutes one loop of the final interacting protein.

Similarly, any number of activation domains may be used for that portion of the prey molecule; such activation domains are preferably weak activation domains, i.e., weaker than the GAL4 activation region II moiety and preferably no stronger than B112 (as measured, e.g., by a comparison with GAL4 activation region II or B112 in parallel β-galactosidase assays using lacz reporter genes); such a domain may, however, be weaker than B112. In particular, the extraordinary sensitivity of the LEU2 selection scheme allows even extremely weak activation domains to be utilized in the invention. Examples of other useful weak activation domains include B17, B42, and the amphipathic helix (AH) domains described in Ma and Ptashne (Cell 51:113, 1987), Ruden et al. (Nature 350:426–430, 1991), and Giniger and Ptashne (Nature 330:670, 1987).

The prey proteins, if desired, may include other optional nuclear localization sequences (e.g., those derived from the GAL4 or MATα2 genes) or other optional epitope tags (e.g., portions of the c-myc protein or the flag epitope available from Immunex). These sequences optimize the efficiency of the system, but are not required for its operation. In particular, the nuclear localization sequence optimizes the efficiency with which prey molecules reach the nuclear-localized reporter gene construct(s), thus increasing their effective concentration and allowing one to detect weaker protein interactions. The epitope tag merely facilitates a simple immunoassay for fusion protein expression.

Those skilled in the art will also recognize that the above-described reporter gene, DNA binding domain, and gene activation domain components may be derived from any appropriate eukaryotic or prokaryotic source, including yeast, mammalian cell, and prokaryotic cell genomes or cDNAs as well as artificial sequences. Moreover, although yeast represents a preferred host organism for the interaction trap system (for reasons of ease of propagation, genetic manipulation, and large scale screening), other host organisms such as mammalian cells may also be utilized. If a mammalian system is chosen, a preferred reporter gene is the sensitive and easily assayed CAT gene; useful DNA binding domains and gene activation domains may be chosen from those described above (e.g., the LexA DNA binding domain and the B42 or B112 activation domains).

Conformation-Constraining Proteins

According to one embodiment of the present invention, the DNA sequence encoding the prey protein is embedded in a DNA sequence encoding a conformation-constraining protein (i.e., a protein that decreases the flexibility of the amino and carboxy termini of the prey protein). Methods for directly linking the amino and carboxy termini of a protein (e.g., through disulfide bonding of appropriately positioned cysteine residues) are described above. As an alternative to this approach, conformation-constraining proteins may be utilized. In general, conformation-constraining proteins act as scaffolds or platforms, which limit the number of possible three dimensional configurations the peptide or protein of interest is free to adopt. Preferred examples of conformation-constraining proteins are thioredoxin or other thioredoxin-like sequences, but many other proteins are also useful for this purpose. Preferably, conformation-constraining proteins are small in size (generally, less than or equal to 200 amino acids), rigid in structure, of known three dimensional configuration, and are able to accommodate insertions of proteins of interest without undue disruption of their structures. A key feature of such proteins is the availability, on their solvent exposed surfaces, of locations where peptide insertions can be made (e.g., the thioredoxin active-site loop). It is also preferable that conformation-constraining protein producing genes be highly expressible in various prokaryotic and eukaryotic hosts, or in suitable cell-free systems, and that the proteins be soluble and resistant to protease degradation. Examples of conformation-constraining proteins useful in the invention include nucleases (e.g., RNase A), proteases (e.g., trypsin), protease inhibitors (e.g., bovine pancreatic trypsin inhibitor), antibodies or rigid fragments thereof, conotoxins, and the pleckstrin homology domain. This list, however, is not limiting. It is expected that other conformation-constraining proteins having sequences not identified above, or perhaps not yet identified or published, may be useful based upon their structural stability and rigidity.

As mentioned above, one preferred conformation-constraining protein according to the invention is thioredoxin or other thioredoxin-like proteins. As one example of a thioredoxin-like protein useful in this invention, $E.\ coli$ thioredoxin has the following characteristics. $E.\ coli$ thioredoxin is a small protein, only 11.7 kD, and can be produced to high levels. The small size and capacity for high level synthesis of the protein contributes to a high intracellular concentration. $E.\ coli$ thioredoxin is further characterized by a very stable, tight tertiary structure which can facilitate protein purification.

The three dimensional structure of $E.\ coli$ thioredoxin is known and contains several surface loops, including a distinctive Cys . . . Cys active-site loop between residues $Cys_{33}$ and $Cys_{36}$ which protrudes from the body of the protein. This Cys . . . Cys active-site loop is an identifiable, accessible surface loop region and is not involved in interactions with the rest of the protein which contribute to overall structural stability. It is therefore a good candidate as a site for prey protein insertions. Human thioredoxin, glutaredoxin, and other thioredoxin-like molecules also contain this Cys . . . Cys active-site loop. Both the amino- and carboxyl-termini of $E.\ coli$ thioredoxin are on the surface of the protein and are also readily accessible for fusion construction. $E.\ coli$ thioredoxin is also stable to proteases, stable in heat up to 80° C. and stable to low pH.

Other thioredoxin-like proteins encoded by thioredoxin-like DNA sequences useful in this invention share homologous amino acid sequences, and similar physical and structural characteristics. Thus, DNA sequences encoding other thioredoxin-like proteins may be used in place of $E.\ coli$ thioredoxin according to this invention. For example, the DNA sequence encoding other species' thioredoxin, e.g., human thioredoxin, are suitable. Human thioredoxin has a three-dimensional structure that is virtually superimposable on *E. coli*'s three-dimensional structure, as determined by comparing the NMR structures of the two molecules. Forman-Kay et al., Biochem. 30:2685 (1991). Human thioredoxin also contains an active-site loop structurally and functionally equivalent to the Cys . . . Cys active-site loop found in the *E. coli* protein. It can be used in place of or in addition to *E. coli* thioredoxin in the production of protein and small peptides in accordance with the method of this invention. Insertions into the human thioredoxin active-site loop and onto the amino terminus may be as well-tolerated as those in *E. coli* thioredoxin.

Other thioredoxin-like sequences which may be employed in this invention include all or portions of the proteins glutaredoxin and various species' homologs thereof (Holmgren, supra). Although *E. coli* glutaredoxin and *E. coli* thioredoxin share less than 20% amino acid homology, the two proteins do have conformational and functional similarities (Eklund et al., EMBO J. 3:1443–1449 (1984)) and glutaredoxin contains an active-site loop structurally and functionally equivalent to the Cys . . . Cys active-site loop of *E. coli* thioredoxin. Glutaredoxin is therefore a thioredoxin-like molecule as defined herein.

In addition, the DNA sequence encoding protein disulfide isomerase (PDI), or that portion containing the thioredoxin-like domain, and its various species' homologs thereof (Edman et al., Nature 317:267–270 (1985)) may also be employed as a thioredoxin-like DNA sequence, since a repeated domain of PDI shares >30% homology with *E. coli* thioredoxin and that repeated domain contains an active-site loop structurally and functionally equivalent to the Cys . . . Cys active-site loop of *E. coli* thioredoxin. The two latter publications are incorporated herein by reference for the purpose of providing information on glutaredoxin and PDI which is known and available to one of skill in the art.

Similarly the DNA sequence encoding phosphoinositide-specific phospholipase C (PI-PLC), fragments thereof, and various species' homologs thereof (Bennett et al., Nature, 334:268–270 (1988)) may also be employed in the present invention as a thioredoxin-like sequence based on the amino acid sequence homology with *E. coli* thioredoxin, or alternatively based on similarity in three dimensional conformation and the presence of an active-site loop structurally and functionally equivalent to Cys . . . Cys active-site loop of *E. coli* thioredoxin. All or a portion of the DNA sequence encoding an endoplasmic reticulum protein, ERp72, or various species homologs thereof are also included as thioredoxin-like DNA sequences for the purposes of this invention (Mazzarella et al., J. Biol. Chem. 265:1094–1101 (1990)) based on amino acid sequence homology, or alternatively based on similarity in three dimensional conformation and the presence of an active-site loop structurally and functionally equivalent to Cys . . . Cys active-site loop of *E. coli* thioredoxin. Another thioredoxin-like sequence is a DNA sequence which encodes all or a portion of an adult T-cell leukemia-derived factor (ADF) or other species homologs thereof (Wakasugi et al., Proc. Natl. Acad. Sci. USA, 87:8282–8286 (1990)). ADF is now believed to be human thioredoxin. Similarly, the protein responsible for promoting disulfide bond formation in the periplasm of *E. coli*, the product of the dsbA gene (Bardwell et al., Cell 67:581–89, 1991) also can be considered a thioredoxin-like sequence. The three latter publications are incorporated herein by reference for the purpose of providing information on PI-PLC, ERp72, ADF, and dsbA which are known and available to one of skill in the art.

It is expected from the definition of thioredoxin-like sequences used above that other sequences not specifically identified above, or perhaps not yet identified or published, may be useful as thioredoxin-like sequences based on their amino acid sequence homology to *E. coli* thioredoxin or based on having three dimensional structures substantially similar to *E. coli* or human thioredoxin and having an active-site loop functionally and structurally equivalent to the Cys . . . Cys active-site loop of *E. coli* thioredoxin. One skilled in the art can determine whether a molecule has these latter two characteristics by comparing its three-dimensional structure, as analyzed for example by x-ray crystallography or two-dimensional NMR spectroscopy, with the published three-dimensional structure for *E. coli* thioredoxin and by analyzing the amino acid sequence of the molecule to determine whether it contains an active-site loop that is structurally and functionally equivalent to the Cys . . . Cys active-site loop of *E. coli* thioredoxin. By "substantially similar" in three-dimensional structure or conformation is meant as similar to *E. coli* thioredoxin as is glutaredoxin. In addition a predictive algorithm has been described which enables the identification of thioredoxin-like proteins via computer-assisted analysis of primary sequence (Ellis et al., Biochemistry 31:4882–91 (1992)). Based on the above description, one of skill in the art will be able to select and identify, or, if desired, modify, a thioredoxin-like DNA sequence for use in this invention without resort to undue experimentation. For example, simple point mutations made to portions of native thioredoxin or native thioredoxin-like sequences which do not effect the structure of the resulting molecule are alternative thioredoxin-like sequences, as are allelic variants of native thioredoxin or native thioredoxin-like sequences.

DNA sequences which hybridize to the sequence for *E. coli* thioredoxin or its structural homologs under either stringent or relaxed hybridization conditions also encode thioredoxin-like proteins for use in this invention. An example of one such stringent hybridization condition is hybridization at 4×SSC at 65° C., followed by a washing in 0.1X SSC at 65° C. for an hour. Alternatively an exemplary stringent hybridization condition is in 50% formamide, 4×SSC at 42° C. Examples of non-stringent hybridization conditions are 4×SSC at 50° C. or hybridization with 30–40% formamide at 42° C. The use of all such thioredoxin-like sequences are believed to be encompassed in this invention.

It may be preferred for a variety of reasons that prey proteins be fused within the active-site loop of thioredoxin or thioredoxin-like molecules. The face of thioredoxin surrounding the active-site loop has evolved, in keeping with the protein's major function as a nonspecific protein disulfide oxido-reductase, to be able to interact with a wide variety of protein surfaces. The active-site loop region is found between segments of strong secondary structure and this provides a rigid platform to which one may tether prey proteins.

A small prey protein inserted into the active-site loop of a thioredoxin-like protein is present in a region of the protein which is not involved in maintaining tertiary structure. Therefore the structure of such a fusion protein is stable. Indeed, *E. coli* thioredoxin can be cleaved into two fragments at a position close to the active-site loop, and yet the tertiary interactions stabilizing the protein remain.

The active-site loop of *E. coli* thioredoxin has the sequence $NH_2$ . . . $Cys_{33}$-Gly-Pro-$Cys_{36}$ . . . COOH. Fusing a selected prey protein with a thioredoxin-like protein in the active loop portion of the protein constrains the prey at both ends, reducing the degrees of conformational freedom of the prey protein, and consequently reducing the number of alternative structures taken by the prey. The inserted prey protein is bound at each end by cysteine residues, which may form a disulfide linkage to each other as they do in native thioredoxin and further limit the conformational freedom of the inserted prey.

In addition, by being positioned within the active-site loop, the prey protein is placed on the surface of the thioredoxin-like protein, an advantage for use in screening for bioactive protein conformations and other assays. In general, the utility of thioredoxin or other thioredoxin-like proteins is described in McCoy et al., U.S. Pat. No. 5,270,181 and LaVallie et al., Bio/Technology 11:187–193 (1993). These two references are hereby incorporated by reference.

There now follows a description of thioredoxin interaction trap systems according to the invention. These examples are designed to illustrate, not limit, the invention.

Thioredoxin Interaction Trap System

Interaction trap systems utilizing conformationally-constrained proteins have been developed for the detection of protein interactions, the identification and isolation of proteins participating in such interactions, the identification and isolation of agonists and antagonists of such interactions, and the identification and isolation of interacting peptide aptamers that may be used in protein detection assays in a manner analogous to antibody-type reagents. Exemplary systems are now described.

1. Thioredoxin Interaction Trap with Cdk2 Bait

Progression of eukaryotic cells through the cell cycle requires the coordinated action of a number of regulatory proteins that interact with and regulate the activity of Cdks (Sherr, Cell 79:551–555 (1994)). These modulatory proteins include cyclins, which positively regulate Cdk activity, Cyclin Dependent kinase inhibitors (Ckis), and a number of protein kinases and phosphatases, some of which, such as CAK and Cdc25, positively regulate kinase activity, some of which, such as Wee1, inhibit kinase activity, and some of which, such as Cdi1 (Gyuris et al., Cell 75:791–803 (1993)), have effects that are so far unknown (reviewed in Morgan, Nature 374:131–134 (1995)). Cdk2 is thought to be required for higher eukaryotic cells to progress from Gi into S-phase (Fang & Newport, J. Cell Biol. 66:731–742 (1991); Pagano et al., J. Cell Biol. 121:101–111 (1993); van den Heuvel & Harlow, Science 262: 2050–2054 (1993)). Cdk2 kinase activity is positively regulated by Cyclin E and Cyclin A (Koff et al., Science 257:1689–1694 (1992); Dulic et al., Science 257:1958–1961 (1992); Tsai et al., Nature 353:174–7 (1991)) and negatively regulated by p21, p27 and p57 (Harper et al., Cell 75:805–816 (1993); Polyak et al., Genes Dev. 8:9–22 (1994); Toyoshima & Hunter, Cell 78:67–74 (1994); Matsuoka et al., Genes Dev. 9:660–662 (1995); Lee et al., Genes Dev. 9:639–649 (1995)); in addition, Cdk2 complexes with Cdi1 at the G1 to S transition (Gyuris et al., supra). Here we describe the use of a yeast two-hybrid system to select molecules which recognize Cdk2 from combinatorial libraries.

Figure 2:
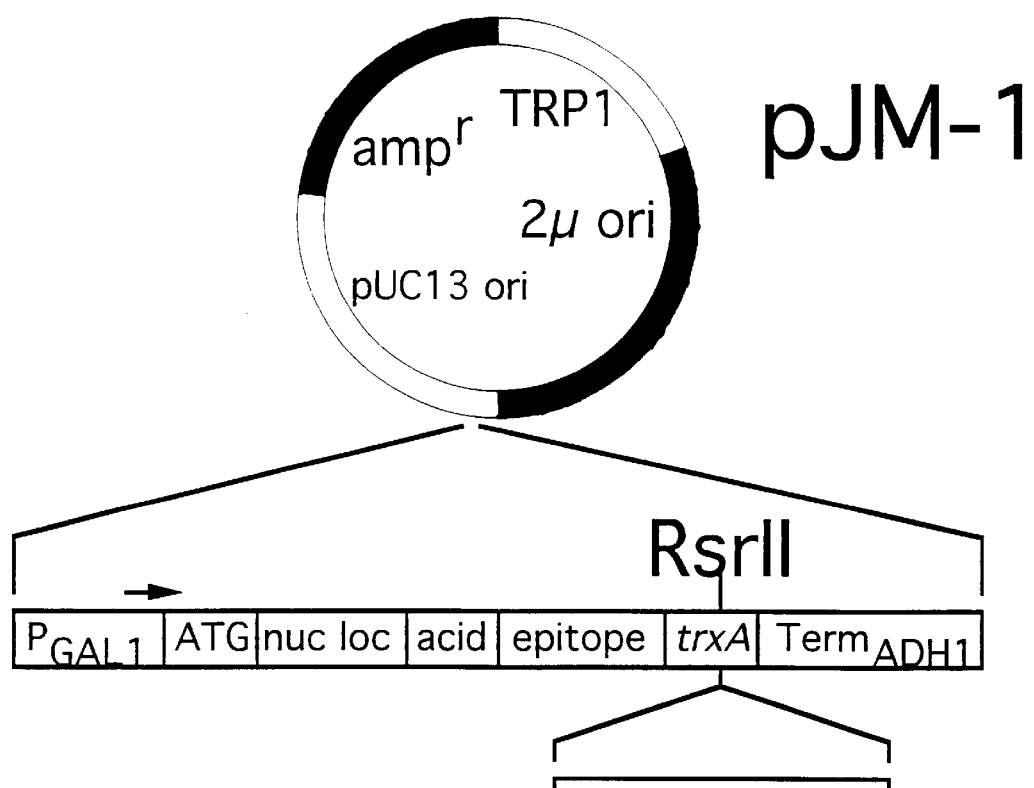
FIG. 2 is a diagram of a library vector pJM1.

A prey vector is constructed containing the E. coli thioredoxin gene (trxA). pJG 4-4 (Gyuris et al., supra) is used as the vector backbone and cut with EcoRI and XhoI. A DNA fragment encoding the B112 transcription activation domain is obtained by PCR amplification of plasmid LexA-B112 (Doug Ruden, Ph.D. thesis, Harvard University, 1992) and cut with MunI and NdeI. The E. coli trxA gene is excised from the vector pALTRXA-781 (U.S. Pat. No. 5,292,646; InVitrogen Corp., San Diego, Calif.) by digestion with NdeI and SalI. The trxA and B112 fragments are then ligated by standard techniques into the EcoRI/XhoI-cut pJG 4-4 backbone, forming pYENAeTRX. This vector encodes a fusion protein comprising the SV40 nuclear localization domain, the B112 transcription activation domain, an hemagglutinin epitope tag, and E. coli thioredoxin (FIG. 2).

Peptide libraries are constructed as follows. The DNA oligomer 5' GACTGACTGGTCCG(NNK)$_{20}$ GGTCCT-CAGTCAGTCAG 3' (with N=A, C, G, T and K=G, T) (SEQ ID NO: 4) is synthesized and annealed to the second oligomer (5' CTGACTGACTGAGGACC 3') (SEQ ID NO: 5) in order to form double stranded DNA at the 3' end of the first oligomer. The second strand is enzymatically completed using Klenow enzyme, priming synthesis with the second oligomer. The product is cleaved with AvaII, and inserted into RsrII cut pYENAeTRX. After ligation, the construct is used to transform E. coli by standard methods (Ausubel et al., Current Protocols in Molecular Biology, (Greene and Wiley-interscience, New York, 1987–1994)). The library contained $2.9\times10^9$ members, of which more than $10^9$ directed the synthesis of peptides. Twenty-mers were chosen as preferred peptides because they were long enough to fold into many different patterns of shape and charge and short enough that many of the encoding oligonucleotides lacked stop codons. Because of the presence of fortuitous restriction sites in some coding oligonucleotides and because some library members contained double inserts, approximately one fifth of the constrained peptides were longer or shorter than unit length.

To screen for interacting peptides or "aptamers," 100 µg of the library was used to transform the yeast strain EGY48 (Mata his3 leu2::2Lexop-LEU2 ura3 trp1 LYS2; Gyuris et al., supra). This strain also contained the reporter plasmid pSH 18–34, a pLR1Δ1 derivative, containing the yeast 2 µ replication origin, the URA3 gene, and a GAL1-lacZ reporter gene with the GAL1 upstream regulatory elements replaced with 4 colE1 LexA operators (West et al., Mol. Cell Biol. 4:2467, 1984; Ebina et al., J. Biol. Chem. 258:13258, 1983; Hanes and Brent, Cell 57:1275, 1989), as well as the bait vector pLexA202-Cdk2 (Cdk2 encodes the human cyclin dependent kinase 2, an essential cell cycle enzyme) (Gyuris et al., supra; Tsai et al., Oncogene 8:1593, 1993). About $2.5\times10^6$ transformants are obtained and pooled. The first selection step, growth on leucine-deficient medium after induction with 2% galactose/1% raffinose (Gyuris et al., supra; Guthrie and Fink, Guide to Yeast Genetics and Molecular Biology, Vol. 194, 1991), was performed with an 8-fold redundancy ($20\times10^6$ cfu) of the library in yeast, and about 900 colonies were obtained after growth at 30° C. for 5 days. The 300 largest colonies were streak purified and tested for the galactose-dependent expression of the LEU2 gene product and of β-galactosidase (encoded by pSH 18–34), the latter giving rise to blue yeast colonies in the presence of Xgal in the medium (Ausubel et al., supra). Thirty-three colonies fulfilled these requirements which, after sequencing, included 14 different clones, all of which bound specifically to a LexA–Cdk2 bait but not to LexA or to a LexA-Cdk3 bait (Finley et al., Proc. Natl. Acad. Sci. USA 91:12980–12984 (1994)). The strength of binding was judged according to the intensity of the blue color formed by a colony of the yeast that contained each different interactor. By this means, each interactor was classified as a strong, medium, or weak binder, which was normalized to the amount of blue color caused by the various naturally-occurring partner proteins of Cdk2 in side by side mating interaction assays. An example of the peptide sequence of one representative of each class is given here:

Strong binder: peptide 3 (SEQ ID NO: 6)
—Gly$_{34}$-Pro$_{35}$-Leu-Val-Cys-Lys-Ser-Tyr-Arg-Leu-Asp-Trp-Glu-Ala-Gly-Ala-Leu-Phe-Arg-Ser-Leu-Phe-Gly$_{34}$-Pro$_{35}$—

Medium binder: peptide 2 (SEQ ID NO: 7)
—Gly$_{34}$-Pro$_{35}$-Met-Val-Val-Ala-Ala-Glu-Ala-Val-Arg-Thr-Val-Leu-Leu-Ala-Asp-Gly-Gly-Asp-Val-Thr-Gly$_{34}$-Pro$_{35}$—

Weak binder: peptide 6 (SEQ ID NO: 8)
—Gly$_{34}$-Pro$_{35}$-Pro-Asn-Trp-Pro-His-Gln-Leu-Arg-Val-Gly-Arg-Val-Leu-Trp-Glu-Arg-Leu-Ser-Phe-Glu-Gly$_{34}$-Pro$_{35}$—

Control peptides which do not bind detectably are: c4: Arg-Arg-Ala-Ser-Val-Cys-Gly-Pro-Leu-Leu-Ser-Lys-Arg-Gly-Tyr-Gly Pro-Pro-Phe-Tyr-Leu-Ala-Gly-Met-Thr-Ala-Pro-Glu-Gly-Pro-Cys (SEQ ID NO: 14) and c: Arg-Arg-Ala-Ser-Val-Cys-Gly-Pro-Leu-His-Tyr-Trp-Gly-Leu-Gly-Gly-Phe-Val-Asp-Leu-Trp-Gln-Glu-Thr-Thr-Gly-Val-Gly-Pro-Cys (SEQ ID NO: 15).

Figure 3A:
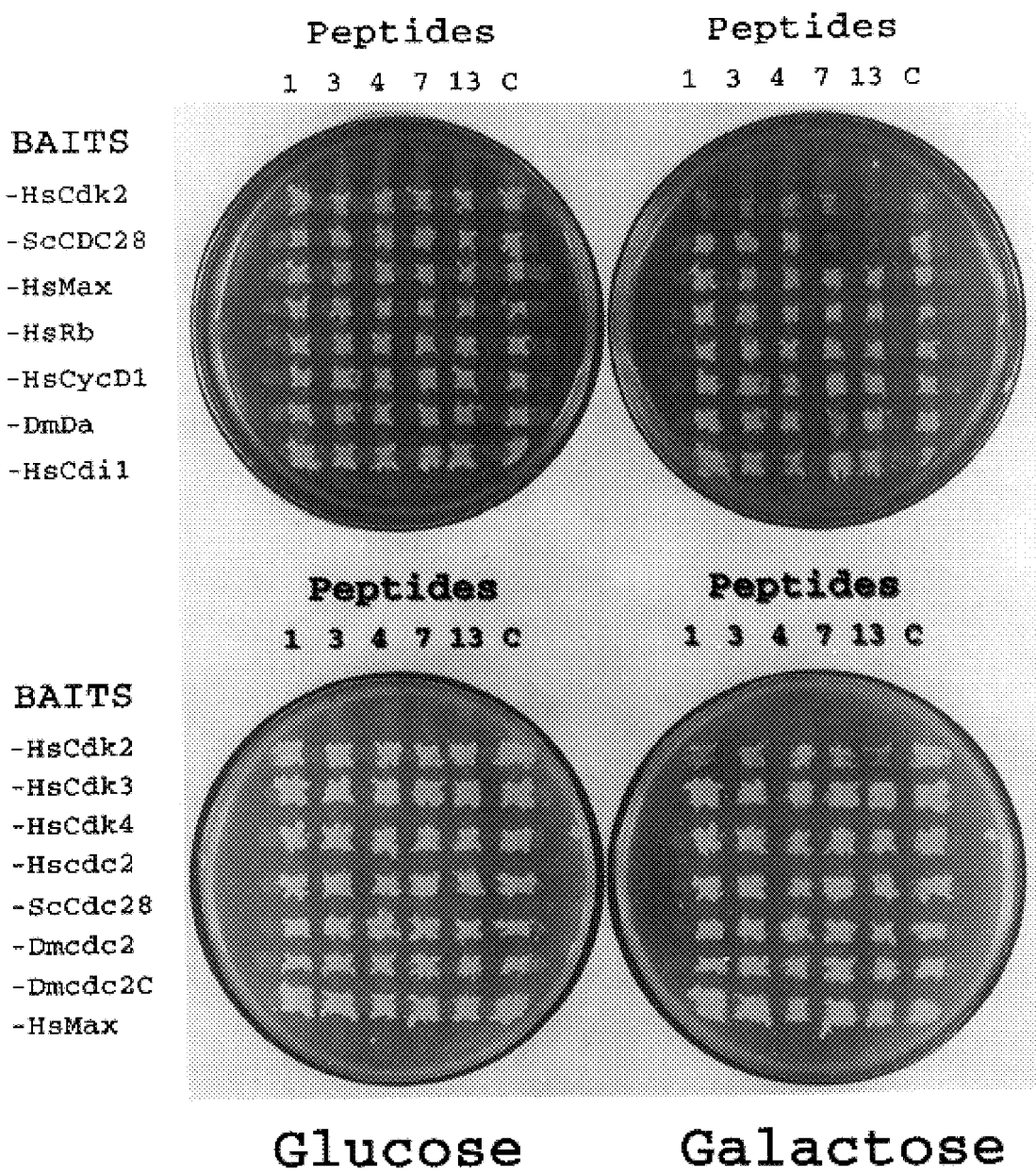
FIG. 3A is a photograph showing the interaction of peptide aptamers with other proteins.

FIG. 3A shows that 5 of the peptide aptamers reacted strongly with the LexA-Cdk2 bait but not with a large number of unrelated proteins. None of the Cdk2 aptamers interacted with CDC28 or Cdc2, which are both 65% identical to Cdk2. However, 2 of the 5 Cdk2 interactors also interacted with human Cdk3, and 1 of the 5 also interacted with Drosophila Cdc2c, suggesting that these peptides recognize determinants common to these proteins. Both theoretical considerations and calibration experiments with lambda repressor's C terminus suggested that transcription of the pSH18-34 reporter in EGY48 can be activated by protein interactions with Kds as weak as $10^{-6}$ M. The fact that peptides 3 and 13 directed robust transcription of the this LexAop-lacZ reporter was consistent with the idea that they may interact significantly more tightly. The sequence of these peptides is shown in FIG. 3B.

Figure 4A:
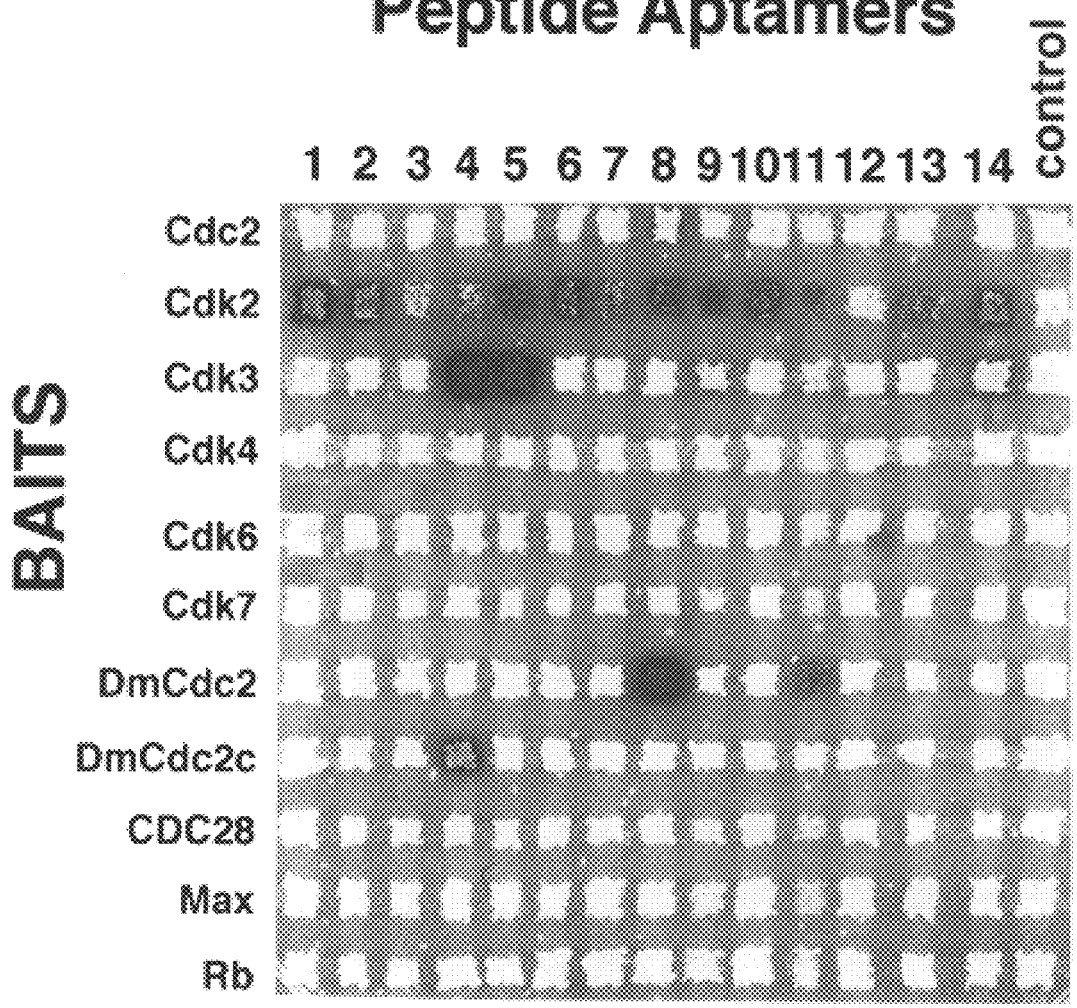
FIG. 4A is a photograph showing the interaction of peptide aptamers with other proteins. The designations of these peptide aptamers differ from those shown in FIG. 3A, and corresponds to the numbering shown in FIG. 4B. To carry out these experiments, yeast strain EGY48 was transformed with either a plasmid expressing an anti-Cdk2 aptamer or with a plasmid expressing a control 20-mer peptide loop, and the strain was then mated to different bait strains as described in Finley et al. (Proc. Natl. Acad. Sci. U.S.A. 91:12980–12984 (1994)).

In related experiments, 6 additional aptamers (i.e., pep6 (SEQ ID NO: 21), pep7 (SEQ ID NO: 22), pep9 (SEQ ID NO: 23), pep12 (SEQ ID NO: 24), pep13 (SEQ ID NO: 25), and pep14 (SEQ ID NO: 26) were shown to interact with the LexA-Cdk2 bait but not with unrelated proteins such as Max or Rb, or with certain Cdk family members such as Cdk4, which shares 47% sequence identity with Cdk2 (FIG. 4A). However, some aptamers interacted with other Cdk family members. The fact that different peptide aptamers showed distinct patterns of cross-reactivity with different Cdks indicated that these aptamers recognized different epitopes conserved among various Cdks. The sequence of the peptide loops is shown in FIG. 4B. Non-unit-length peptides occurred at the same frequency among the Cdk2 interacting aptamers as in the library as a whole. No aptamer showed significant sequence similarity to known proteins, as expected if the 20-mer peptides indeed formed novel recognition structures. All of the peptides were charged, suggesting that some of their interactions with the Cdk2 target could be ionic.

To confirm the specificity of the Cdk2 interaction, a Gst-Cdk2 fusion protein was immobilized on glutathione sepharose beads, and these beads were used to specifically precipitate bacterially expressed peptide aptamers. One set of results is shown in FIG. 5, and another set in FIG. 6.

Figure 5:
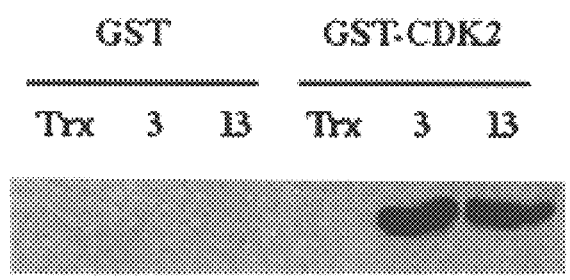
FIG. 5 illustrates coprecipitation of peptides 3 and 13 by Gst-Cdk2. Lane 1. Gst Beads, extract contains TrxA; Lane 2. Gst Beads, extract contains TrxA-peptide 3; Lane 3. Gst Beads, extract contain TrxA-peptide 13; Lane 4. Gst-Cdk2 beads, extract contains TrxA; Lane 5. Gst-Cdk2 beads, extract contains TrxA-peptide 3; and Lane 6. Gst-Cdk2, extract contains TrxA-peptide 13.

For the FIG. 5 results, Gst-Cdk2 was expressed in E. coli and purified on glutathione sepharose as previously described (Lee et al., Nature 374:91–94 (1995)). The peptides were generated as follows: fragments that directed the synthesis of peptides 3 and 13 were made by PCR amplification of the insert encoded by the corresponding library plasmid and introduced into pAL-TrxA (LaVallie et al., supra). Fusion proteins were expressed and lysed in a French pressure cell as previously described (LaVallie et al., supra). Coprecipitation was carried out using Gst-Sepharose beads as described in Lee et al. (supra), and samples were run on 15% SDS polyacrylamide gels and transferred to nylon membranes. TrxA-containing fusion proteins were visualized by probing the membranes with an anti-TrxA antibody, followed by treatment of the immobilized antibody with peroxidase-coupled anti-rabbit IgG antibody ECL reagents according to the manufacturer's instructions (Amersham, Arlington Heights, Ill.).

Figure 6:
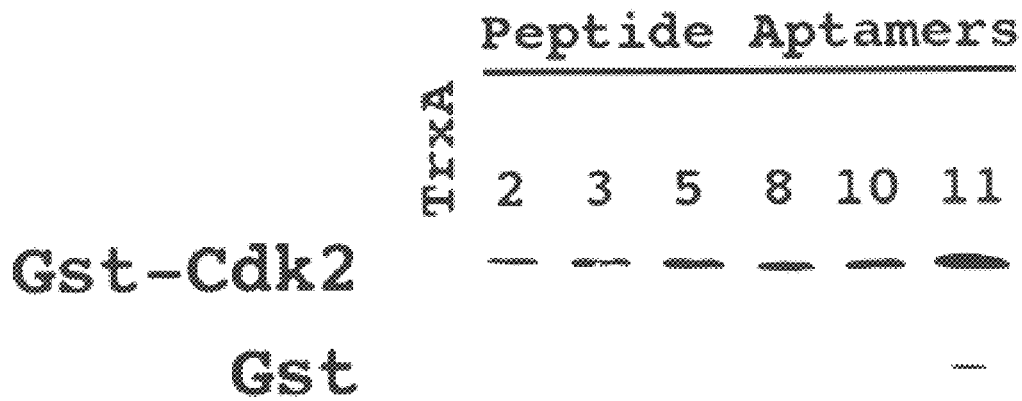
FIG. 6 illustrates coprecipitation of the peptide aptamers of FIGS. 4A and 4B.

For the FIG. 6 results, Gst and Gst-Cdk2 were purified as described (Lee et al., Nature 374:91–94 (1995)). pALHIS-TRX was constructed by annealing the oligonucleotides 5' TAATGAGCGATAAACACCACCACCAC-CACCACGACGACGACGACAAAGG3' (SEQ ID NO: 27) and 5' TACCTTTGTCGCTGTCGTCGTGGTGGTG-GTGGTGGTGTTTATCGCTCATTA3' (SEQ ID NO: 28), and ligating into NdeI-cut pALTRX-781 (LaVallie et al., supra). AvaII fragments encoding peptide loops were then cloned from the library plasmids into RsrII-cut PALHIS-TRX. His6-TrxA and His6-aptamers were expressed in GI724 as previously described (Ausubel et al., supra), the proteins were purified on $Ni^{2+}$-NTA-Agarose according to manufacturer's directions (Qiagen, Chatsworth, Calif.), and then dialyzed against 10mM Hepes pH 7.4/50 mM NaCl. 1 µg of His6-TrxA or His6-aptamers was precipitated with Gst or Gst-Cdk2 sepharose beads as described (Lee et al., supra), and the products detected by Western blot analysis with an anti-TrxA rabbit antiserum and ECL reagents (Amersham, Arlington Heights, Ill.).

The results shown in FIGS. 5 and 6 demonstrated that the interactions between Cdk2 and the peptide aptamers could be observed in vitro, and were thus independent of any bridge proteins native to yeast.

To determine the binding affinities of these aptamers for Cdk2, the following experiments were carried out. Based on interpolation from interaction trap calibration experiments (Estojak et al., Mol. Cell. Biol. 15:5820–5829 (1995)), the robust transcription that some of the aptamers of FIGS. 4A and 4B directed from the pSH18–34 reporter suggested that the equilibrium dissociation constants (Kds) of the interactions was <$10^{-6}$ M. In order to precisely measure the binding affinity of the aptamers to Cdk2, we used an evanescent wave instrument (BIAcore, Pharmacia, Piscataway, N.J.). Purified His6-Cdk2 was coupled to CM-dextran chips, and peptide aptamers flowed in running buffer over the chips. Following binding, the chips were rinsed with running buffer lacking aptamer.

In particular, in these experiments, HIS6-Cdk2 was cross-linked in 11 mM MES pH 6.1/50 mM NaCl to CM5 chips with an amine-coupling kit (Pharmacia, Piscataway, N.J.). Purified aptamers were then flowed in running buffer (Hepes 10 mM pH 7.4/50 mM NaCl) onto the chips at 5 µl/minute, and association and dissociation of the His6-Cdk2-aptamer complexes recorded as variations in resonance angle with time. Association phase started upon aptamer injection, and dissociation phase upon running buffer injection. Portions of association and dissociation curves were then fitted that excluded the sudden variations in resonance angle caused by transitions between running buffer and aptamer-containing running buffer, which differed slightly in refractive index ("buffer fluxes").

Figure 7:
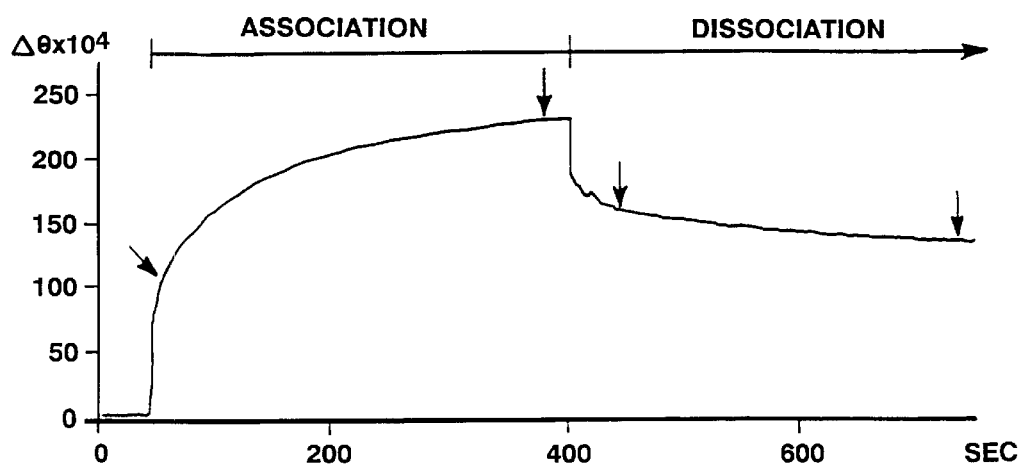
FIG. 7 illustrates a representative binding affinity graph produced using an evanescent wave instrument.

Association and dissociation rate constants were determined by fitting the association and dissociation phases of at least two runs (and typically four runs) for each aptamer to exponential functions using the data analysis Program IGOR (Wavemetrics, Inc., Lake Oswego, Org.) and a non-linear least squares algorithm as described in O'Shannessy et al. (Anal. Biochem. 212:457–468 (1993). Kds were calculated by dividing dissociation rate constants by association rate constants. A representative wave instrument run is shown in FIG. 7, and Table 1 indicates that, under the conditions described above, all aptamers exhibited Kds between 30 and 120 nM.

TABLE 1

| Aptamer | Dissociation rate constant ×10⁻⁶ (s⁻¹) | Association rate constant (M⁻¹s⁻¹) | Kd (nM) |
| --- | --- | --- | --- |
| Pep 2 | 480 +/−109 | 7474 +/−270 | 64 +/−12 |
| Pep 3 | 246 +/−20 | 2201 +/−160 | 112 +/−1 |
| Pep 5 | 428 +/−16 | 8263 +/−215 | 52 +/−1 |
| Pep 8 | 120 +/−15 | 3122 +/−23 | 38 +/−5 |
| Pep 10 | 693 +/−64 | 6555 +/−28 | 105 +/−10 |
| Pep 11 | 484 +/−25 | 5590 +/−168 | 87 +/−7 |

The ability to select TrxA-peptides that interact specifically with designated intracellular baits allows for the creation of other classes of intracellular reagents. For example, appropriately derivitized TrxA-peptide fusions may allow the creation of antagonists or agonists (as described above). Alternatively, peptide fusions allow for the creation of homodimeric or heterodimeric "matchmakers," which force the interaction of particular protein pairs. In one particular example, two proteins are forced together by utilizing a leucine zipper sequence attached to a conformation-constraining protein containing a candidate interaction peptide. This protein can bind to both members of a protein pair of interest and direct their interaction. Alternatively, the "matchmaker" may include two different sequences, one having affinity for a first polypeptide and the second having affinity for the second polypeptide; again, the result is directed interaction between the first and second polypeptides. Another practical application for the peptide fusions described herein is the creation of "destroyers," which target a bound protein for destruction by host proteases. In an example of the destroyer application, a protease is fused to one component of an interacting pair and that component is allowed to interact with the target to be destroyed (e.g., a protease substrate). By this method, the protease is delivered to its desired site of action and its proteolytic potential effectively enhanced. Yet another application of the fusion proteins described herein are as "conformational stabilizers," which induce target proteins to favor a particular conformation or stabilize that conformation. In one particular example, the ras protein has one conformation that signals a cell to divide and another conformation that signals a cell not to divide. By selecting a peptide or protein that stabilizes the desired conformation, one can influence whether a cell will divide. Other proteins that undergo conformational changes which increase or decrease activity can also be bound to an appropriate "conformational stabilizer" to influence the property of the desired protein.

2. Functional Inhibition of Cdk2

To determine whether Cdk2 interacting peptides might inhibit Cdk2 function in vivo, we took advantage of the fact that human Cdk2 can complement temperature sensitive alleles of Cdc28 (Elledge and Spottswood, EMBO 10:2653–2659, 1991; Ninomiya et al., PNAS 88:9006–9010, 1991; Meyerson et al., EMBO 11:2909–2917, 1992). Peptide 13 inhibits the plating efficiency of a Cdk2-dependent yeast. A strain carrying the temperature sensitive cdc28-1N mutation can form colonies at high temperature if it carries a plasmid that expresses Cdk2. At the restrictive temperature, compared to the plating efficiency of yeast expressing control peptides, expression of peptide 13 diminishes the plating efficiency of this strain by 10-fold. Both peptide 3 and 13 have similar effects on the plating efficiency at 37° C. of a Cdk2(+) strain that carries the cdc28-13ts allele.

Expression of peptide 13 slows the doubling time of a Cdk2(+), cdc28ts-1N strain by a factor of 50%. Microscopic examination of strains expressing the peptide revealed that a high proportion of these cells had an elongated morphology characteristic of cdc28-1N cells at the restrictive temperature, whereas cells expressing a control peptide had a more normal morphology.

Peptide 13 does not affect the growth of a cdc28-1Nts strain at high temperature when the defect is complemented by a plasmid expressing wild-type Cdc28 product, and has no effect on yeast at the permissive temperature. While we do not intend to be bound by any particular theory, it appears that this peptide blocks yeast cell cycle progression by binding to some face of the Cdk2 molecule and inhibiting its function and thereby interfering with its ability to interact with cyclins, other partners, or with substrates.

In later experiments with the aptamers of FIG. 4B, inhibition of Cdk2 activity by these peptides (for example, by binding to a face of the molecule and by blocking its interaction with one of its partner proteins or substrates) was examined. In particular, the ability of the aptamers to inhibit phosphorylation of Histone Hi by Cdk2/Cyclin E kinase was tested. To carry out these experiments, $2 \times 10^7$ Sf9 cells were co-infected with recombinant bacculoviruses expressing hemagglutinin-tagged Cdk2 and His6-Cyclin E as described (Kato et al., Genes & Dev. 7:331–342 (1993); Desai et al., Mol. Biol. Cell 3:571–582 (1992)). Cells were lysed 40 hours after infection in 500 $\mu$l of 1×Kinase Buffer (Kato et al., supra), and 5 $\mu$l of a 100-fold diluted extract was used in 30 $\mu$l reactions. Reactions were carried out for 20 minutes at 25° C. by adding 2.5 $\mu$Ci of [$\gamma^{32}$P] ATP (3000 Ci/mmol), 25 $\mu$M ATP, 100 ng of Histone H1 (Sigma, St. Louis, Mo.), and varying amounts of His6-TrxA or His6-aptamers. Samples were run on 15% SDS-PAGE gels and exposed by autoradiography.

Figure 8:
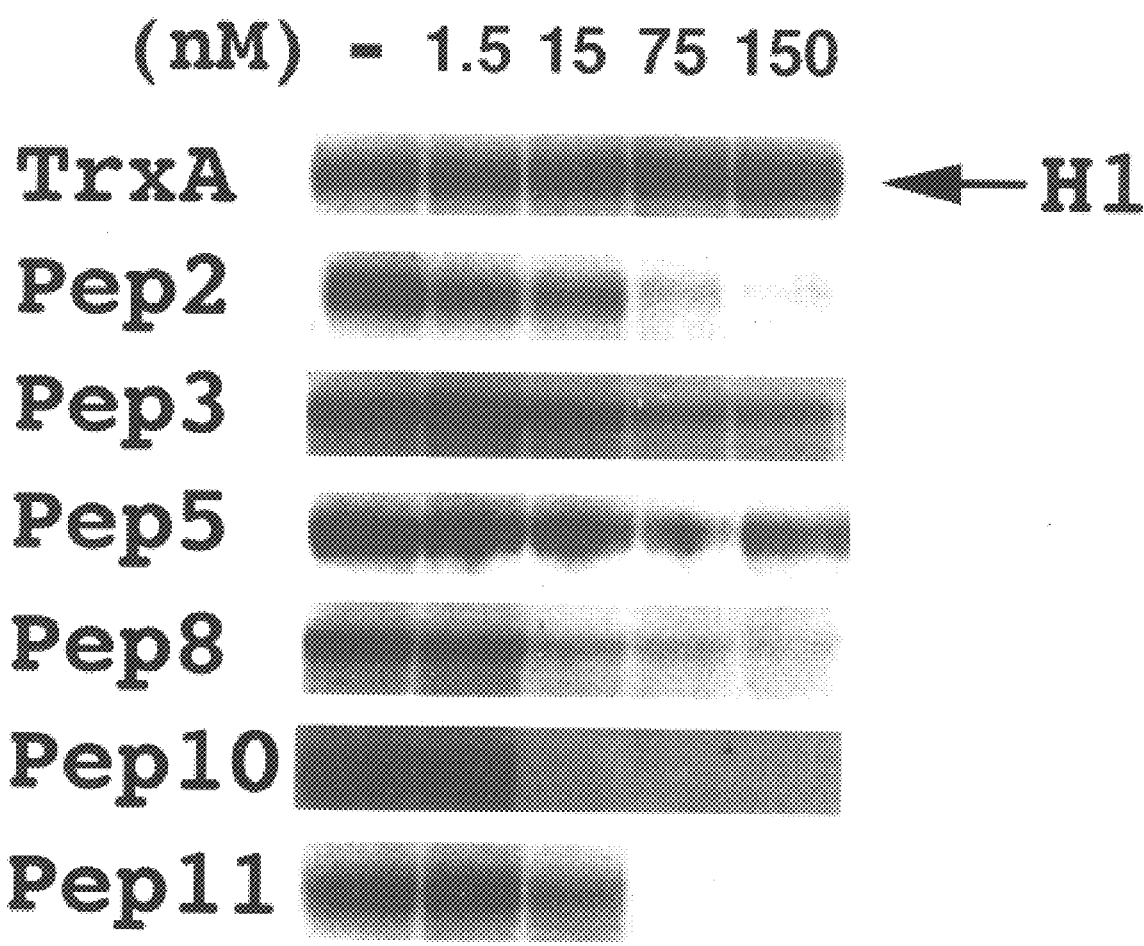
FIG. 8 illustrates the ability of exemplary peptide aptamers of FIGS. 4A and 4B to inhibit phosphorylation of Histone H1 by Cdk2/cyclin E kinase.

The results of these experiments are shown in FIG. 8. All tested aptamers were able to inhibit phosphorylation of Histone H1 by Cdk2/Cyclin E kinase. Under standard conditions (pH 7.5, 0 mM NaCl) (Kato et al., supra), apparent half-inhibitory concentrations ranged from 1.5 to 100 nM. To rule out the possibility that a trace bacterial contaminant was responsible for the inhibition, we removed the His6-peptide aptamer from the Pep2 preparation with a rabbit polyclonal anti-thioredoxin antiserum; this immunodepleted preparation no longer inhibited Cdk2 kinase activity. Half-inhibitory concentrations of aptamers were lower than the Kds measured from evanescent wave experiments, consistent with the idea that some of the energy of each interaction is ionic and is reduced by the salt in the evanescent wave instrument running buffer.

In co-precipitation experiments (Reymond et al., Oncogene 11:1173–1178 (1995)), purified Pep2 did not compete with in vitro-translated cyclin E for binding to in vitro-translated Cdk2. However, inhibition by Pep2 was reversed by addition of a 10-fold excess of Histone H1, suggesting that at least Pep2 inhibits kinase activity by competing with its H1 substrate.

Previous studies have established that libraries of unconstrained peptides contain sequences capable of recognizing targets in vitro (Devlin et al., Science 249:404–406 (1990); Cwirla et al., Proc. Natl. Acad. Sci. USA 87:6378–6382

(1990); Lam et al., Nature 354:82–84 (1991); Songyang et al., Current Biology 4:973–982 (1994); Scott et al., Current Biology 5:40–48 (1994)) and in yeast (Yang et al., Nucl. Acids. Res. 23:1152–1156 (1995)); such isolated peptide sequences often bear similarity to natural interactors. By contrast, although constrained peptide libraries are less conformationally diverse (McConnell et al., Gene 151:115–118 (1994)), the lack of conformational diversity should lower the entropic cost if binding causes the loop to adopt a single conformation (Spolar et al., Science 263:777–784 (1994)); this reduction in entropic cost may account for the fact that our Cdk2 peptide aptamers recognize their targets with higher affinity than is typically observed for unconstrained peptides (Yang et al., supra; Oldenburg et al., Proc. Natl. Acad. Sci. USA 89:5393–5397 (1992); McLafferty et al., Gene 128:29–36 (1993)). This high affinity suggests that peptide aptamers may inhibit protein function in vivo, in the simplest case by binding to specific faces of the target molecule and disrupting its interaction with specific partners or effectors.

The ability to generate large numbers of aptamers from combinatorial libraries, taken together with the interaction trap, which offers a powerful selection for those that bind specific proteins, facilitates the selection of peptide aptamers against a variety of intracellular targets. Aptamers which inhibit protein contacts can be used to aid the dissection of the networks of protein interactions that govern division of higher eukaryotic cells and can also be used for the genetic analysis of those metazoan organisms for which isolation of specific missense alleles may be impractical. The analogy of the aptamers of the invention with antibodies indicates that peptide aptamers can also be used in other applications in which immunological reagents are now employed, such as ELISAs, immunofluorescence experiments, and sensors. If desired, the affinity of these aptamers may be increased, for example, by increasing their valency and using existing interaction technology to select mutants that bind more tightly. This first generation of peptide aptamers facilitates the production of recognition modules for intracellular nano-technologies aimed at destroying, modifying, and assembling macromolecules inside cells.

3. Thioredoxin Interaction Trap with OncoRas Bait

The ras proteins are essential for many signal transduction pathways and regulate numerous physiological functions including cell proliferation. The ras genes were first identified from the genome of Harvey and Kirsten sarcoma virus. The three types of mammalian ras genes (N-, K-ras, and H-ras) encode highly conserved membrane-bound guanine nucleotide binding proteins with a molecular mass of 21 kDa, which cycle between the active (GTP-bound) form and the inactive (GDP-bound) form.

In normal cells, the active form of Ras is short-lived, as its intrinsic GTPase activity rapidly converts the bound-GTP to GDP. The GTPase activity is stimulated $10^5$-fold by GTPase-activating proteins (GAPs). GTP-bound Ras interact with GAP, c-Raf, neurofibromatosis type 1 (NF-1) and Ral guanine nucleotide dissociation stimulator (RalGDS).

Mutationally-activated RAS proteins are found in about 30% of human tumor cells and have greatly decreased GTPase activity which can not be stimulated by GAPs. The majority of mutations studied thus far are due to a point mutation at either residue Gly-12 or residue Gln-61 of Ras. These Ras mutants remain in the active form and interact with the downstream effectors to result in tumorigenesis. It has been shown that there are significant conformational differences between GTP-bound forms of wild-type and oncogenic RAS proteins. Such conformational differences are likely causes for malignant transformation induced by oncogenic ras proteins.

Such mutationally-activated conformational changes in GTP-bound H-ras mutants provide targets for members of a conformationally constrained random peptide library. In the present example, the library is a conformationally constrained thioredoxin peptide library, as described above. Library members, which interact with oncogenic Ras have been identified using a variation of the interaction trap technology provided above. The oncogenic Ras peptide aptamers isolated may be assayed for their ability to disrupt the interaction of oncogenic Ras with known effectors and to inhibit cellular transformation.

We have used well-characterized oncogenic H-ras(G12V) for isolation and characterization of its peptide aptamers. Peptide aptamers for other oncogenes can be isolated using adaptations of this protocol as provided herein.

Bait Construction

Figure 9:
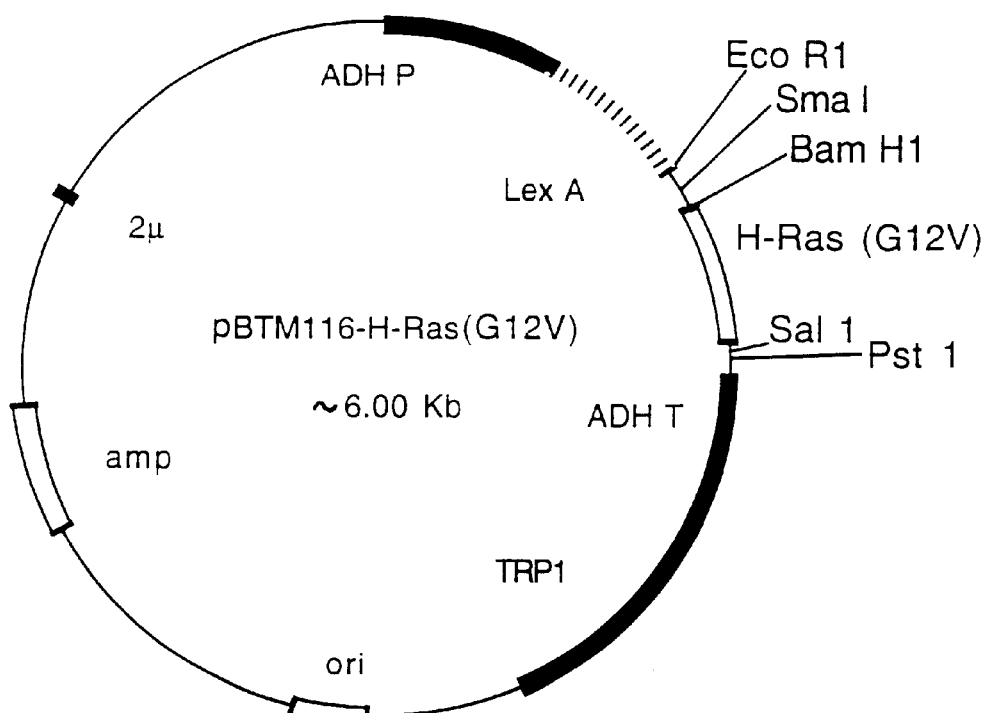
FIG. 9 illustrates the vector BRM116-H-Ras(G12V).
Figure 10:
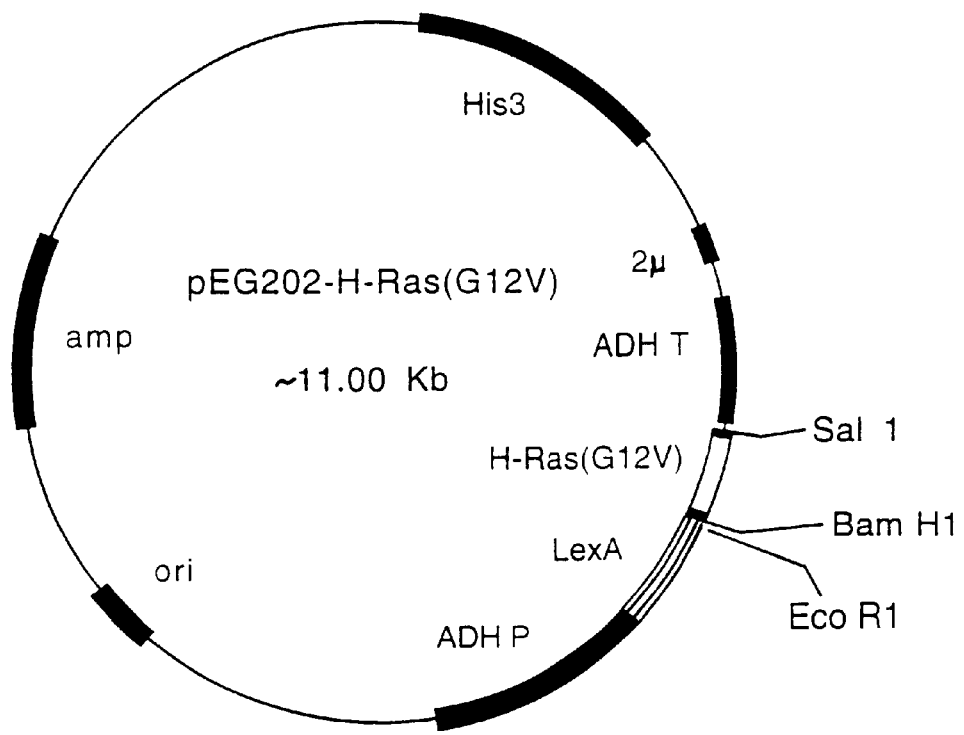
FIG. 10 illustrates the vector pEG202-H-Ras(G12V).

Construction of LexA-Ras(G12V)/pEG202:H-Ras(G12V) DNA was performed by digesting BTM116-H-Ras (G12V) (FIG. 9) with BamHI and SalI. H-Ras(G12V) DNA was ligated with pEG202 backbone digested with BamHI and SalI. The resulting plasmid was called pEG202-H-Ras(G12V) (or V6) (FIG. 10). Screening for H-Ras(G12V) peptide aptamers pEG202-H-Ras(G12V) (V6) was transformed into the EGY48 strain according to a standard yeast transformation protocol; in particular, the protocol provided by Zymo Research (Orange County, Calif.) was used here. EGY48 was grown in YPD medium to $OD_{600}$=0.2–0.7. Cells were pelleted at 500× g for 4 min. and resuspended in 10 ml of EZ1 solution (Zymo Research). The cells were then pelleted by centrifugation and resuspended in 1 ml of EZ2 (Zymo Research). Aliquots of competent cells (50 μl) were stored in a −70° C. freezer.

An aliquot of competent cells was mixed with 0.1 μg of LexA-H-Ras(G12V)/pEG202 and 500 μl of EZ3 solution (Zymo Research). The mixture was incubated at 30° C. for 30 min. and plated onto a yeast medium lacking histidine and uracil. One colony was picked and inoculated into 100 ml of glucose Ura-His- medium at 30° C. with shaking (150 rpm) until the $OD_{600}$ measurement was 0.96. The culture was centrifuged at 2000 g for 5 min and cell pellets were resuspended in 5 ml of sterile LiOAc/TE. The cells were again centrifuged as above and resuspended in 0.5 ml of sterile LiOAc/TE.

Aliquots (50 μl) of the cells were then incubated at 30° C. for 30 min. with 1 μg of thioredoxin peptide library DNA, 70 μg of salmon sperm DNA, and 300 μl of sterile 40% PEG 4000 in LiOAc/TE. The mixtures were heat-shocked at 42° C. for 15 min. Each aliquot was plated onto a 24 cm×24 cm plate containing glucose Ura-His-Trp- medium and was incubated at 30° C. for two days. The transforming efficiency typically ranged from 50,000 to 100,000 colony forming units per μg of library DNA.

A total of 1.5 million transformants were obtained and were plated onto the selection medium of galactose/raffinose Leu-Ura-His-Trp-. Of the 338 colonies formed, among them 50 were randomly picked and inoculated into 5 ml of glucose Leu-Ura-His-Trp- medium for preparation of yeast plasmid DNA. A half ml of each yeast culture was mixed with an equal volume of acid-washed sand and phenol/chloroform/isoamyl alcohol (24:24:1), and vortexed in a vortexer for 2 min. The mixture was then centrifuged for 15 min., and the supernatant was precipitated with ethanol. DNA pellets were resuspended in 50 μl of TE.

One μl of each sample was used to transform *E. coli* KC8 cells by electroporation. Bacterial transformants were selected on minimal agar supplemented with uracil, leucine, histidine, and ampicillin. Each type transformant resulted in final isolation of plasmid which a leucine marker, which carries a DNA fragment encoding thioredoxin-peptide fusion protein.

Sequence determination of the 50 isolates was carried out according to the directions of the fmolDNA™ sequencing systems (Promega, Madison, Wis.) using primer 5'-GACGGGGCGATCCTCGTCG-3' (SEQ ID NO:16). Nine out of 50 isolates (referred to as #4, #18, #39, #41, #22, #24, #30, #31, #46) contained unique peptide encoding sequences, as determined by electrophoresis of the dT/ddT termination reaction. Among them, the predicted peptide aptamer sequence of #39 is as follows:

Trp-Ala-Glu-Trp-Cys-Gly-Pro-Val-Cys-Ala-His-Gly-Ser-Arg-Ser-Leu-Thr-Leu-Leu-Thr-Lys-Tyr-His-Val-Ser-Phe-Leu-Gly-Pro-Cys-Lys-Met-Ile-Ala-Pro-Ile-Leu-Asp (SEQ ID NO:17). From our results, it appears that approximately 60 unique H-Ras(G12V) peptide aptamers (338×9/50) were isolated in the first round of screening.

OTHER EMBODIMENTS

As described above, the invention features a method for detecting and analyzing protein-protein interactions. Typically, in the above experiments, the bait protein is fused to the DNA binding domain, and the prey protein (in association with the conformation-constraining protein) is fused to the gene activation domain. The invention, however, is readily adapted to other formats. For example, the invention also includes a "reverse" interaction trap in which the bait protein is fused to a gene activation domain, and the prey protein (in association with a conformation-constraining protein) is fused to the DNA binding domain. Again, an interaction between the bait and prey proteins results in activation of reporter gene expression. Such a "reverse" interaction trap system, however, depends upon the use of prey proteins which do not themselves activate downstream gene expression.

The protein interaction assays described herein can also be accomplished in a cell-free, in vitro system. Such a system may begin with a DNA construct including a reporter gene operably linked to a DNA-binding-protein recognition site (e.g., a LexA binding site). To this DNA is added a bait protein (e.g., any of the bait proteins described herein bound to a LexA DNA binding domain) and a prey protein (e.g., one of a library of conformationally-constrained candidate interactor prey proteins bound to a gene activation domain). Interaction between the bait and prey protein is assayed by measuring the reporter gene product, either as an RNA product, as an in vitro translated protein product, or by some enzymatic activity of the translated reporter gene product. Alternatively, interactions involving conformationally constrained proteins may be carried out by direct in vitro techniques, for example, by any standard physical or biochemical technique for identifying protein interactions (such as immobilization of a first protein on a column or other solid support and contact with a conformationally-constrained protein). These direct in vitro approaches are preferably carried out in such a way that the DNA encoding the confromationally-constrained protein may be readily isolated, for example, by using techniques involving phage display or display of the protein on the E. coli flagella.

These in vitro systems may also be used to identify agonists or antagonists, simply by adding to a known pair of interacting proteins (in the above described system) a candidate agonist or antagonist interactor and assaying for an increase or decrease (respectively) in reporter gene expression, as compared to a control reaction lacking the candidate compound or protein. To facilitate large scale screening, candidate prey proteins or candidate agonists or antagonists may be initially tested in pools, for example, of ten or twenty candidate compounds or proteins. From pools demonstrating a positive result, the particular interacting protein or agonist or antagonist is then identified by individually assaying the components of the pool. Such in vitro systems are amenable to robotic automation or to the production of kits. Kits including the components of any of the interaction trap systems described herein are also included in the invention.

In one particular embodiment, interacting proteins identified in vitro are tested for their ability to interact in vivo. Such in vivo interacting proteins may be used for any diagnostic or therapeutic purpose. For example, proteins shown to interact in vivo may be used to disrupt, encourage, or stablize intracellular interactions or may be used as an intracellular antibody-type reagent.

The components (e.g., the various fusion proteins or DNA therefor) of any of the in vivo or in vitro systems of the invention may be provided sequentially or simultaneously depending on the desired experimental design.

Other embodiments are within the following claims.

What is claimed is:

1. A method for detecting a first protein in a sample comprising (a) contacting said sample with a second protein having reduced structural flexibility due to non-naturally-occurring recombinantly-introduced disulfide bonding between cysteine residues at said second protein's amino- and carboxy-termini, said contacting being carried out under conditions which allow said second protein to specifically bind to said first protein and form a complex; and (b) detecting said complex.

2. A method of assaying an interaction between a first protein and a second protein, comprising:

(a) providing said first protein;

(b) providing a fusion protein comprising said second protein, said second protein having reduced structural flexibility due to disulfide bonding between cysteine residues at said second protein's amino- and carboxy-termini;

(c) contacting said first protein with said fusion protein under conditions which allow complex formation;

(d) detecting said complex; and (e) determining whether said first protein interacts with said fusion protein inside a cell by the steps of:

(i) providing a host cell which contains (a) a reporter gene operably linked to a DNA-binding-protein recognition site; (b) said first protein covalently boned to a DNA binding protein which specifically binds to said DNA-binding-protein recognition site; and (c) said second protein covalently bonded to a gene activating moiety; and (ii) measuring expression of said reporter gene as a measure of an interaction between said first protein and said second protein.

3. The method of claim 2, wherein said cysteine residues at said second protein's amino- and carboxy-termini are recombinantly introduced.

4. A method of assaying an interaction between a first protein and a second protein, comprising:

(a) providing said first protein;

(b) providing a fusion protein comprising said second protein, said second protein having reduced structural flexibility due to covalent bonding of both the amino and carboxy termini of said second protein to a conformation-constraining protein;

(c) contacting said first protein with said fusion protein under conditions which allow complex formation;

(d) detecting said complex; and (e) determining whether said first protein interacts with said fusion protein inside a cell by the steps of:

(i) providing a host cell which contains (a) a reporter gene operably linked to a DNA-binding-protein recognition site; (b) said first protein covalently bonded to a DNA binding protein which specifically binds to said DNA-binding-protein recognition site; and (c) said second protein covalently bonded to a gene activating moiety; and (ii) measuring expression of said reporter gene as a measure of an interaction between said first protein and said second protein.

5. The method of claim 4, wherein said second protein is embedded within said conformation-constraining protein.

6. The method of claim 4, wherein said conformation-constraining protein is thioredoxin.

7. The method of claim 4, wherein said conformation-constraining protein is a thioredoxin-like molecule, said thioredoxin-like molecule being characterized by having a three-dimensional structure substantially similar to that of human or *E. coli* thioredoxin and containing an active site loop.

8. The method of claim 6, wherein said second protein is inserted into the active site loop of said thioredoxin.

9. The method of claim 7, wherein said active site loop has a structure substantially similar to that of human or *E. coli* thioredoxin or glutaredoxin.

10. A method for detecting a first protein in a sample, comprising (a) contacting said sample with a second protein having reduced structural flexibility due to covalent bonding of both the amino- and carboxy-termini of said second protein to a thioredoxin-like molecule, said thioredoxin-like molecule having a three-dimensional structure substantially similar to that of human or *E. coli* thioredoxin and containing an active site loop, said first protein or said second protein being an intracellular protein, said contacting being carried out under conditions which allow said second protein to specifically bind to said first protein and form a complex; and (b) detecting said complex.

11. The method of claim 10, wherein said thioredoxin-like molecule is thioredoxin.

12. The method of claim 11, wherein said second protein is inserted into the active site loop of said thioredoxin.

13. The method of claim 10, wherein said active site loop has a structure substantially similar to that of human or *E. coli* thioredoxin or glutaredoxin.

14. The method of claim 10, wherein said second protein is embedded within said thioredoxin-like protein.

15. The method of claim 4 or 10, wherein said detecting step is carried out by an immunoprecipitation, Western blot, or affinity column technique that utilizes said second protein having reduced structural flexibility as the complex-forming reagent.

16. The method of claim 1 or 2, wherein said detecting step is carried out by an immunoprecipitation, Western blot, or affinity column technique that utilizes said second protein having reduced structural flexibility as the complex-forming reagent.

17. The method of claim 1, 2, or 4, wherein said first protein or said second protein is an intracellular protein.

18. The method of claim 1, 2, 4, or 10, wherein said second protein is a peptide of at least 6 amino acids.

19. The method of claim 1, 2, 4, or 10, wherein said second protein is a peptide of less than or equal to 60 amino acids in length.

20. The method of claim 1, 2, 4, or 10, wherein said second protein comprises a randomly generated or intentionally designed peptide sequence.

* * * * *

UNITED STATES PATENT AND TRADEMARK OFFICE
CERTIFICATE OF CORRECTION

PATENT NO. : 6,399,296 B1
DATED : June 4, 2002
INVENTOR(S) : Roger Brent, John M. McCoy, Timm H. Jessen and Chanxing Wilson Xu It is certified that error appears in the above-identified patent and that said Letters Patent is hereby corrected as shown below:

Title page,
Item [57], ABSTRACT,
Line 16, after "interactions." add -- Proteins isolated by these methods are also discussed. Finally, populations of eukaryotic cells are disclosed, each cell having a recombinant DNA molecule encoding a conformationally-constrained intracellular peptide. --

Column 17,
Line 43, delete "Gi" and insert -- G1 --.

Column 18,
Line 32, delete "Mata" and insert -- Matα --.

Column 20,
Line 51, delete "11mM" and insert -- 10mM --.

Column 22,
Line 28, delete "Hi" and insert -- H1 --.
Line 59, delete "cyclin E" and insert -- Cyclin E --.

Column 24,
Line 40, delete "Ura-His-" and insert -- Ura$^-$His$^-$ --.
Line 51, delete "Ura-His-Trp" and insert -- Ura$^-$His$^-$Trp$^-$ --.
Lines 57 and 59, delete "Leu-Ura-His-Trp" and insert -- Leu$^-$Ura$^-$His$^-$Trp$^-$ --.

UNITED STATES PATENT AND TRADEMARK OFFICE
CERTIFICATE OF CORRECTION

PATENT NO.    : 6,399,296 B1
DATED         : June 4, 2002
INVENTOR(S)   : Roger Brent, John M. McCoy, Timm H. Jessen and Chanxing Wilson Xu It is certified that error appears in the above-identified patent and that said Letters Patent is hereby corrected as shown below:

<u>Column 39,</u>
Line 2, delete "sample" and insert -- sample, --.
Line 29, delete "boned" and insert -- bonded --.

Signed and Sealed this

Nineteenth Day of November, 2002

*Attest:*

*Attesting Officer*

JAMES E. ROGAN
*Director of the United States Patent and Trademark Office*